(12) United States Patent
Littell

(10) Patent No.: US 10,791,982 B2
(45) Date of Patent: Oct. 6, 2020

(54) METHODS OF MEASURING HEAD, NECK, AND BRAIN FUNCTION AND PREDICTING AND DIAGNOSING MEMORY IMPAIRMENT

(71) Applicant: Stephanie Littell, Lexington, MA (US)

(72) Inventor: Stephanie Littell, Lexington, MA (US)

(*) Notice: Subject to any disclaimer, the term of this patent is extended or adjusted under 35 U.S.C. 154(b) by 977 days.

(21) Appl. No.: 15/306,811

(22) PCT Filed: May 1, 2015

(86) PCT No.: PCT/US2015/028826
§ 371 (c)(1),
(2) Date: Oct. 26, 2016

(87) PCT Pub. No.: WO2015/168579
PCT Pub. Date: Nov. 5, 2015

(65) Prior Publication Data
US 2017/0049377 A1    Feb. 23, 2017

Related U.S. Application Data

(60) Provisional application No. 62/092,580, filed on Dec. 16, 2014, provisional application No. 61/987,626, filed on May 2, 2014.

(51) Int. Cl.
*A61B 5/00*    (2006.01)
*A61B 5/026*   (2006.01)
(Continued)

(52) U.S. Cl.
CPC ........... *A61B 5/4088* (2013.01); *A61B 5/021* (2013.01); *A61B 5/0261* (2013.01); *A61B 5/031* (2013.01);
(Continued)

(58) Field of Classification Search
CPC . A61B 5/4088; A61B 5/14553; A61B 5/7271; A61B 5/14546; A61B 5/021;
(Continued)

(56) References Cited

U.S. PATENT DOCUMENTS 7,231,240 B2 * 6/2007 Eda ................. A61B 5/14553
600/322
9,402,546 B2 * 8/2016 Segman ................. A61B 5/411
(Continued)

OTHER PUBLICATIONS

International Preliminary Report on Patentability, issued in PCT/US2015/028826, entitled "Methods of Measuring Head, Neck, and Brain Function and Predicting and Diagnosing Memory Impairment,", dated Nov. 17, 2016.
(Continued)

*Primary Examiner* — Eric F Winakur
(74) *Attorney, Agent, or Firm* — Hamilton, Brook, Smith & Reynolds, P.C.

(57) ABSTRACT

A computer based method and system forms measurements of brain function and predictions of a likelihood for memory impairment via the use of cameras, including a near-infrared (NIR) spectroscopic device and a camera capturing images in the Red-Green-Blue (RGB) spectrum. The device acquires from a subject measurements of ions, molecules, or combinations thereof at more than one moment in time, as well as amplitude and timing of blood pulsations. Based on the measured molecule or ion concentration, flow, and so forth, a processor assesses the probability of a neuron to form an action potential. Formation of an action potential increases the probability that the subject individual will create a memory.

23 Claims, 18 Drawing Sheets

(51) Int. Cl.
*A61B 5/021* (2006.01)
*A61B 5/03* (2006.01)
*A61B 5/1455* (2006.01)
*A61B 5/145* (2006.01)
*A61B 5/16* (2006.01)

(52) U.S. Cl.
CPC ............ *A61B 5/032* (2013.01); *A61B 5/1455* (2013.01); *A61B 5/14546* (2013.01); *A61B 5/14553* (2013.01); *A61B 5/168* (2013.01); *A61B 5/6814* (2013.01); *A61B 5/6898* (2013.01); *A61B 5/7271* (2013.01); *A61B 5/742* (2013.01); *A61B 5/746* (2013.01)

(58) Field of Classification Search
CPC ....... A61B 5/031; A61B 5/0261; A61B 5/032; A61B 5/6814; A61B 5/6898; A61B 5/742; A61B 5/746
See application file for complete search history.

(56) References Cited

U.S. PATENT DOCUMENTS

| | | |
|---|---|---|
| 2004/0039268 A1 | 2/2004 | Barbour et al. |
| 2007/0219439 A1 | 9/2007 | Vilser et al. |
| 2008/0287821 A1* | 11/2008 | Jung .................. G06F 19/3418 600/544 |
| 2009/0143654 A1 | 6/2009 | Funanc et al. |
| 2009/0247853 A1 | 10/2009 | Debreezeny |
| 2010/0292545 A1* | 11/2010 | Berka .................... A61B 5/163 600/301 |
| 2012/0150257 A1 | 6/2012 | Aur et al. |
| 2013/0190556 A1* | 7/2013 | Wetmore .............. A61M 21/02 600/28 |
| 2013/0322729 A1 | 12/2013 | Mestha et al. |

OTHER PUBLICATIONS

International Search Report, "Methods of Measuring Head, Neck, and Brain Function and Predicting and Diagnosing Memory Impairment," PCT/US2015/028826, dated May 2, 2014.

Written Opinion of the International Searching Authority, "Methods of Measuring Head, Neck, and Brain Function and Predicting and Diagnosing Memory Impairment," PCT/US2015/028826, dated Oct. 2, 2015.

Strangman et al., "Non-Invasive Neuroimaging Using Near-Infrared Light", Biol Psychiatry, 2002, 52:679-693 (Exhibit B).

Saddawi-Konefka and Bryner, Chapter 1—Dissolved Oxygen in the Blood and Chapter 2—Bound Oxygen in the Blood, accessed on Oct. 23, 2014, http://www.umich.edu/~projbnb/cvr/o2.html, 10 pages (Exhibit C).

White et al., "Laboratory Spectra of $CO_2$ Vibrational Modes in Planetary Ice Analogs", Icarus, 2012, 221:1032-1042 (Exhibit D).

Huber et al., "Carbonic Acid Revisited: Vibrational Spectra, Energetics and the Possibility of Detecting an Elusive Molecule", AIP Advances 2012; 2: 032180 (Exhibit E).

Siermann and Gilmour, "Hydronium Ion Absorption in the Region 1.7μ", Can. J. Chem. 1959, 37:1249-1253 (Exhibit F).

* cited by examiner

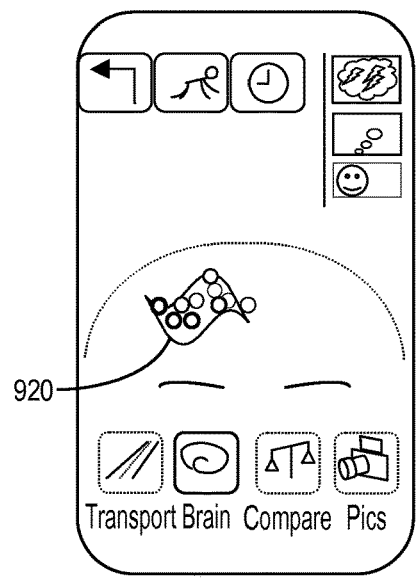
FIG. 9C
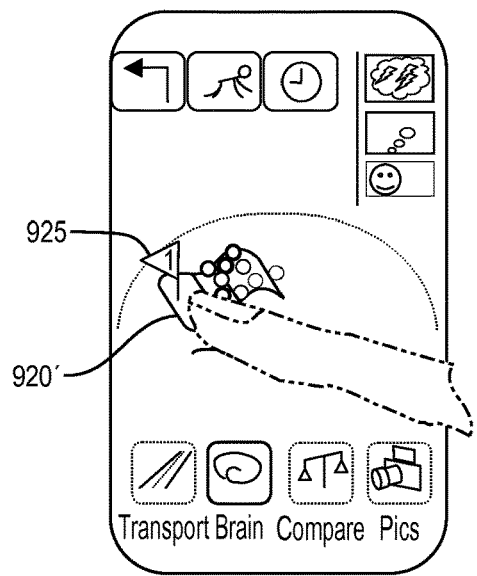
FIG. 9D
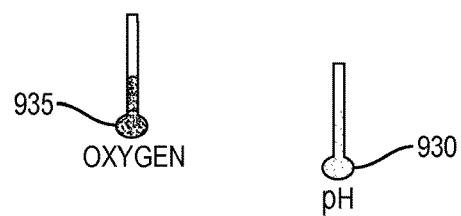
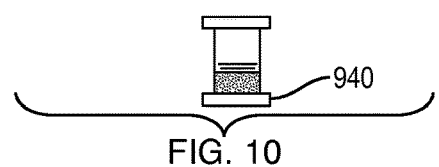
FIG. 10

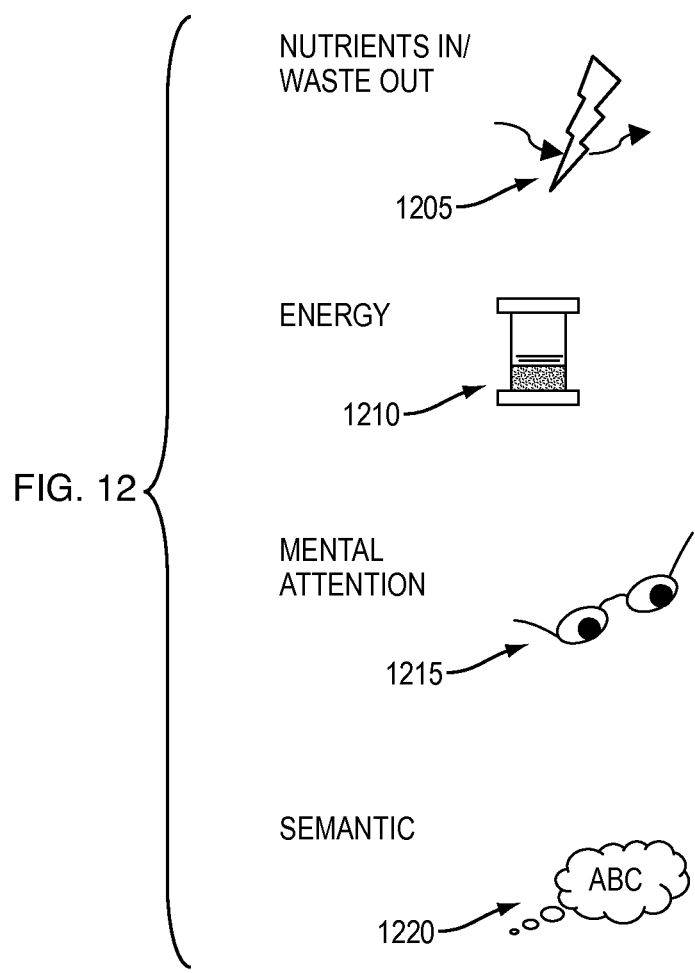

METHODS OF MEASURING HEAD, NECK, AND BRAIN FUNCTION AND PREDICTING AND DIAGNOSING MEMORY IMPAIRMENT

RELATED APPLICATIONS

This application is the U.S. National Stage of International Application No. PCT/US2015/028826, filed May 1, 2015, which designates the U.S., published in English, and claims the benefit of U.S. Provisional Application No. 62/092,580, filed Dec. 16, 2014 and which claims the benefit of U.S. Provisional Application No. 61/987,626, filed May 2, 2014. The entire teachings of the above applications are incorporated herein by reference.

BACKGROUND OF THE INVENTION

Maintaining a healthy brain is critical to overall health and well-being. Early detection of disease or other threats to brain health permits individuals to seek treatment sooner and, ideally, provides individuals with a greater chance of reversal or prevention of further declines in brain health.

Memory impairment and memory loss can be a result of multiple etiologies. Commonly, Alzheimer's disease is a cause of memory loss. However, short-term or long-term memory loss may be caused by a number of other diseases and syndromes, such as medications, drugs, trauma, infections, dementia, depression, age-related, and stroke. Progression of memory loss or memory impairment can be unsettling and debilitating. It is emotionally difficult for a person having memory loss or impairment, and such memory loss interferes with daily life. Memory loss or impairment ranges from the occasional forgetfulness (for example, where car keys were placed, whether medications were taken), to lack of recognition of friends and family members.

Memory impairment and memory loss also affects spouses, family members, relatives and friends who witness first-hand mental and cognitive decline.

Typically, Alzheimer's disease is clinically diagnosed based on family history and behavioral observations in a patient, for example assessed through neuropsychological tests. Certain other cerebral pathologies can be ruled out via MRI or CT imaging technologies. Definitive biological diagnoses of Alzheimer's disease are currently possible only upon autopsy and analysis of brain tissue, however, certain biomarkers for Alzheimer's disease allow for a probable diagnosis. Amyloid protein plaques, for example, are a biomarker of Alzheimer's disease and are detectable in cerebral spinal fluid.

An adequate supply of oxygen and nutrients is critical for normal brain function. Blood carrying oxygenated hemoglobin and nutrients is delivered to the brain through the vascular system, whereby pulsations of blood travel from the heart, through the carotid and vertebral arteries, and ultimately through capillaries where the exchange of water, oxygen, carbon dioxide and other nutrients occurs between the blood and nearby tissues. Decreased blood flow to a region of the brain may result in impairment of that brain region's function. The interruption of blood flow to a region of the brain of an individual may indicate that the individual has suffered a stroke, a condition for which immediate medical attention is required, even in the absence of outward physical symptoms.

Frequently, medical attention for the diagnosis and treatment of illnesses related to brain function is not sought until after the manifestation of physical symptoms, such as memory loss, impairment of speech, loss of consciousness, numbness, and paralysis. In the absence of timely medical attention, lasting disabilities or death may occur. The ability to visualize the vasculature and circulatory function of the brain is not accessible to the average individual, except through imaging studies conducted by medical professionals, and, as stated above, individuals frequently delay seeking medical attention until after the onset of physical symptoms.

Therefore, there is a need for improved methods to monitor brain function, health, and memory, and particularly for methods which are accessible to the average individual. Additionally, there is a need to detect decreased or interrupted blood flow before the onset of physical symptoms. There is also a need for improved methods to predict and diagnose a patient's level of memory impairment and cognitive ability, and track a patient's memory loss or impairment over time.

SUMMARY OF THE INVENTION

The present invention relates to methods of monitoring and visualizing the vasculature system and circulatory function of the brain, as well as other characteristics, enabling individuals to monitor their own brain health. The present invention also relates to methods of alerting individuals without significant medical knowledge of potentially adverse changes in their circulatory function in an easily comprehensible manner, prompting them to seek early medical attention, if needed. The present invention further relates to methods of predicting and diagnosing memory impairment in an individual and to determining and monitoring the ability of an individual to form new memories. In addition, the present invention relates to computer systems and devices that aid in the monitoring of brain function, health, and memory.

Accordingly, in one embodiment, the invention is directed to a method for predicting a likelihood for memory impairment in an individual. The method includes using a near infrared spectroscopic device on an individual at an anatomical region to be studied. The method also includes determining, with the device at the anatomical region, a first measurement of each of one or more ions, one or more molecules, or combinations thereof at a first time. The method further includes determining a second measurement of each of the one or more ions, one or more molecules, or combinations thereof at a second time, and comparing the first measurement to the second measurement of each of the one or more ions, one or more molecules or combinations thereof. The method further includes determining, based on the comparison step, a probability for one or more neurons to generate an action potential, wherein the generation of an action potential increases the probability of totaling a new memory, thereby predicting (or totaling a prediction of) the likelihood for memory impairment in the individual.

Another embodiment of the invention is directed to a computer system to predict a likelihood for memory impairment in an individual. The computer system includes a measuring module configured to determine a first measurement of each of one or more ions, one or more molecules, or combinations thereof at a first time and configured to determine a second measurement of each of the one or more ions, one or more molecules, or combinations thereof at a second time. The computer system further includes a comparison module configured to compare the first measurement to the second measurement of each of the one or more ions, one or more molecules or combinations thereof. The computer system further includes a probability module coupled to the comparison module and configured to determine a probability for one or more neurons to generate an action potential, wherein the generation of an action potential increases the probability of forming a new memory, thereby predicting, or forming a prediction of, the likelihood for memory impairment in the individual.

The first time, at which the first measurement is determined, can be a first moment or a first time interval, and the second time, at which the second measurement is determined, can be a second moment or a second time interval.

The method can include establishing a baseline from one or more measurements of one or more ions, molecules, or combinations thereof at the first time. In certain embodiments, the computer system further includes a baseline module configured to establish a baseline from one or more measurements of the one or more ions, molecules, or combinations thereof at the first time. The baseline can represent a memory map, e.g., a local memory map, of the individual.

The method can include normalizing the memory map based on the individual's age, gender, or other characteristic. In certain embodiments, the computer system includes a normalization module configured to normalize the memory map. The measuring module can include a baseline submodule and/or a normalization submodule.

The method can include assessing hypoxia, acidosis, decreased ion flux, or combinations thereof, based on steps of the method for predicting a likelihood for memory impairment. The computer system can include an assessment module configured to assess hypoxia, acidosis, decreased ion flux, or combinations thereof. In some embodiments, a presence of hypoxia, acidosis, decreased ion flux, or combinations thereof relates to an increased likelihood of memory impairment. The comparison module and/or probability module can be formed of or otherwise includes the assessment module.

In embodiments of the method and computer system of the present invention, the presence of hypoxia is determined by a measured oxygen concentration ($PaO_2$), a measured oxygen saturation ($O_2$ sat), a measured arterial oxygen content ($CaO_2$), a measured hemoglobin (Hb) concentration, or combinations thereof.

In embodiments of the method and computer system of the present invention, the presence of acidosis is determined by a measured concentration of hydrogen ($H^+$), bicarbonate ($HCO_3^-$), carbonic acid ($H_2CO_3$), $CO_2$, phosphate ($PO_4^{3-}$, $HPO_4^{2-}$, $H_2PO_4^-$, $H_3PO_4$) or combinations thereof.

In embodiments of the method and computer system of the present invention, the measured ion comprises hydrogen ($H^+$), sodium ($Na^+$), potassium ($K^+$), calcium ($Ca^{2+}$), magnesium ($Mg^{2+}$), chloride ($Cl^-$), carbonate ($CO_3^-$), bicarbonate ($HCO_3^-$), or a phosphate ($H_3PO_4$, $H_2PO_4^-$, $HPO_4^{2-}$, or $PO_4^{3-}$).

In embodiments of the method and computer system of the present invention, the measured molecule comprises a nucleic acid, an amino acid, a sugar, a protein, a fatty acid, a nucleoside, a nucleotide, or combinations thereof.

The protein can be hemoglobin; the amino acid can be any one of glutamate and gamma-aminobutyric acid (GABA).

In other embodiments, the method includes measuring cerebral blood pressure, cerebral blood flow, cerebrospinal fluid pressure, cerebrospinal fluid flow, intracranial pressure, or combinations thereof. In certain embodiments, the computer system includes or the measuring module includes a second measuring module configured to measure cerebral blood pressure, cerebral blood flow, or combinations thereof.

In certain embodiments, the anatomical region includes a forehead of the individual. In other embodiments, the region comprises a frontal, parietal, limbic, occipital, or temporal lobe of the individual.

In certain embodiments, the computer system includes a device module configured to connect one or more infrared spectroscopic devices. The device module can be operatively part of the measuring module.

In embodiments of the method and computer system of the present invention, the infrared spectroscopic device is a portable device, such as a cell phone, tablet, phablet, laptop computer, wearable aid, for example, a wristwatch, wrist cuffs, or footwear. The device can also be a stand-alone device or at least one mountable sensor that can be placed onto a body, or embedded into clothing, bedding, or other devices. In certain embodiments, the infrared spectroscopic device includes a built-in camera and software for measuring the one or more ions, one or more molecules, or combinations thereof.

In another embodiment, the invention is directed to a computer-implemented method of measuring and displaying brain circulatory function in an individual. The method includes using a camera of a mobile device to capture a sequence of images at an anatomical region of an individual, utilizing a digital processor associated with the mobile device to process the captured images to obtain volumetric, frequency, magnetic, and cycle time information related to the pulsation and flow of fluid through the vessels and cavities of the anatomical region of the individual, and to analyze the information to obtain functional features relating to the individual's brain circulatory system. The method further includes rendering a graphical representation of the functional features of the individual's brain circulatory system on a screen of the mobile device.

In another embodiment, the invention is directed to a mobile device for measuring and displaying brain, face, and neck circulatory function in an individual. The mobile device can include a camera configured to capture a sequence of images of an anatomical region of an individual, a digital processor, and a screen configured to render a graphical representation of functional features of the individual's brain circulatory system. The digital processor can be configured to process the images to obtain volumetric, frequency, magnetic, and cycle time information in relation to the pulsation and flow of fluid through the vessels and cavities of the individual, and to analyze such information to obtain functional features of the individual's brain circulatory system.

In embodiments of the method and device of the present invention, the invention is directed to acquiring images in the RGB (red-green-blue) visible light spectrum to capture images of the vasculature of the face, head and neck. In another embodiment, the invention is directed to acquiring images in the near infrared spectrum to capture images of the vasculature beneath the skull. The invention is also directed towards deducing functional features of the vasculature including a frequency of blood pulsations through a vessel, a volumetric change of a vessel, a concentration of oxygenated hemoglobin, a concentration of deoxygenated hemoglobin, rate of oxygen dissociation, and rate of nutrient diffusion across a blood brain barrier. The mobile device of the invention may be a wearable aid, cell phone, tablet, laptop computer, or mountable sensor(s), for non-limiting example. Other mobile or portable devices are suitable. The functional features can be computed for each of a bilateral subsection of the individual's anatomy and the functional features of each of the subsections can be compared to assess a circulatory deficiency of the individual. A cyclic vessel wall displacement, a vessel volume, cyclic pressure, an angular velocity and a corresponding wave energy can be estimated. The individual can be alerted to a circulatory deficiency.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIGS. 9A-9D are schematic illustrations of user interfaces for displaying representations of electrical brain activity.

FIG. 10 includes illustrations of easily-comprehensible figures/icons representing pH, oxygen rippling, and energy.

FIG. 12 illustrates spin-pointer options.

DETAILED DESCRIPTION OF THE INVENTION

Figure 1:
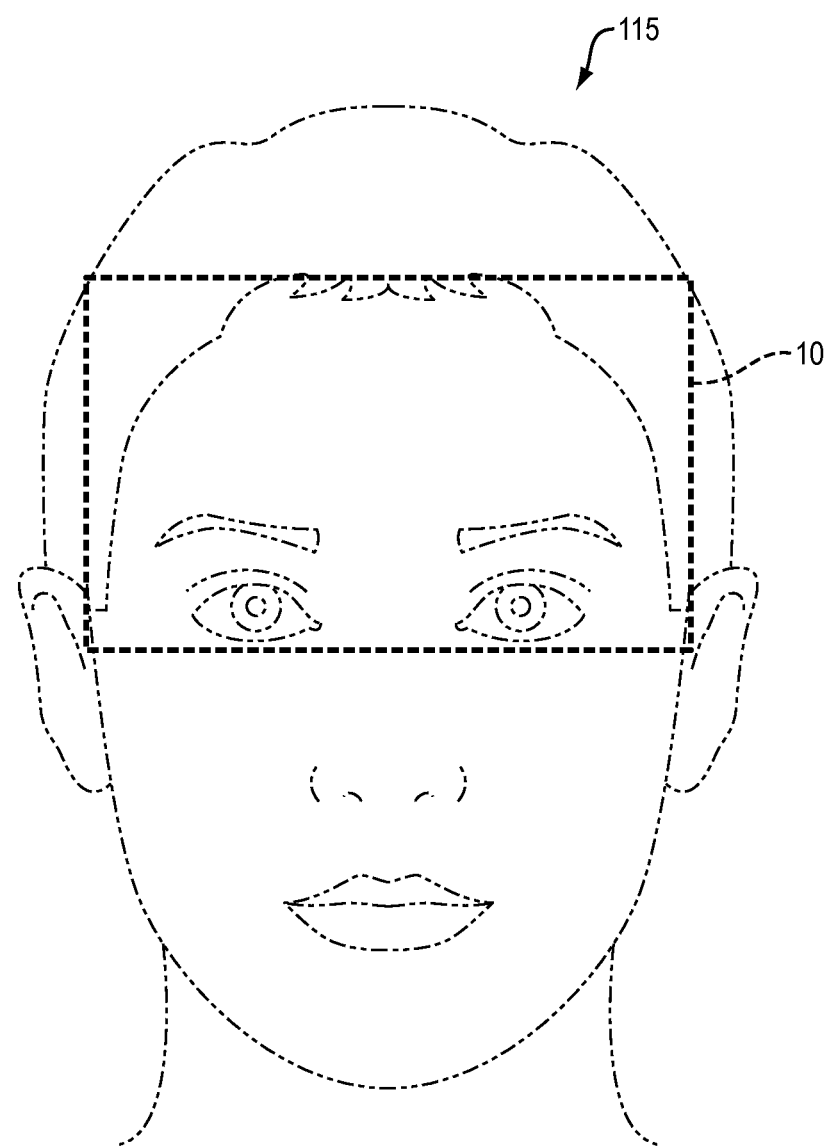
FIG. 1 is a schematic view of embodiments measuring a head and/or face area of an individual.

A description of example embodiments of the invention follows.

The generation of an action potential is required for the formation of a memory in humans (mammals generally). Therefore, in order to assess the ability of an individual to form a memory, or alternately, in order to assess the likelihood for memory impairment in an individual, the embodiments of the present invention provide methods and apparatus for assessing the probability of a neuron to generate an action potential.

Accordingly, in one embodiment, the invention is directed to a method, systems and apparatus for predicting a likelihood for memory impairment in an individual. An embodiment 100 illustrated in FIGS. 1 and 2 includes using a near infrared spectroscopic device on an individual (step 115 of FIG. 2) at an anatomical region 10 to be studied. The computer-based system 100 is initialized for the individual at 111 and started at 113 of FIG. 2. The system 100 at step or module 117 determines, with the device at the anatomical region 10, a first measurement of each of one or more ions, one or more molecules, or combinations thereof at a first time. Measuring module or step 117 further determines a second measurement of each of the one or more ions, one or more molecules, or combinations thereof at a second time, and a comparison module or step 123 compares the first measurement to the second measurement of each of the one or more ions, one or more molecules or combinations thereof. The system/method 100 (through a series of steps 119-125) assesses and eventually determines 127, based on the comparison at 123, a probability for one or more neurons to generate an action potential. The generation of an action potential increases the probability of forming a new memory, and thereby is a predictor of or forms a prediction of the likelihood for memory impairment in the individual. Step 129 stores an indication of the prediction (evaluation results) 127 as a local-to-regional memory map.

"Memory impairment" as used herein, means any problem with an individual's memory (e.g., a decline in an individual's ability to form new memories or ability to recall formed memories). Memory impairment can also refer to a deficit that is beyond the scope of what would be anticipated or predicted in the normal course of aging. Memory impairment can be assessed based on clinical observation, neuroimaging, neuropsychological testing, and so forth. In certain embodiments, an individual's memory impairment is compared against, or fit into a spectrum of memory impairment observed in other individuals, as stored in a library 120 for example. Such multi-dimensional fitting could be stored in the final memory evaluation 129 and used for further external processing. Such a comparison, or such a spectrum, can include an analysis of age, gender, education level, profession, physical fitness, past medical history, or other characteristics of an individual. In other embodiments, memory impairment is compared to or assessed against (in module or step 127) another measurement or prediction of memory impairment of the same individual, taken at an earlier time point, for example, five years prior.

In certain embodiments, the time at which module or step 117 takes a measurement of ions, molecules, or a combination thereof is a moment in time. In certain other embodiments, the time is an interval of time. The interval of time can be selected based on nutrient influx (e.g., Hb—O), or, alternatively, by arterial pulse cyclicality as indicated or otherwise provided at 122.

An infrared spectroscopic device of module/step 115 measures energy in the near-infrared (NIR) region of the electromagnetic spectrum (energy having a wavelength from about 650 nm to about 1400 nm). In certain embodiments, the device is portable. A spectroscopic device of 115 can be connected to, or be part of an electronic processing device (e.g., cell phone, tablet, laptop computer, portable digital processor device, or handheld computer) 50 of FIGS. 13 and 14. In certain other embodiments the spectroscopic device at 115 further comprises a screen display or monitor. In other embodiments, the spectroscopic device 115, 50 comprises a module for emailing or uploading data to a server 60 (FIG. 13), a computer connected to the Internet 70 (FIG. 13), or a printer (or similar I/O devices). In other embodiments, the spectroscopic device 50, 115 comprises a camera and programmed processor for measuring one or more ions, one or more molecules, or combinations thereof.

The anatomical region 10 that is studied in the methods and systems of the present invention can lie anywhere along the surface of the head as schematically shown in FIG. 1. In certain embodiments, it is most efficient to begin with the prefrontal cortex, which is often furthest from the cardiovascular supplying arteries. The prefrontal cortex also contains the highest-level integration of neuronal information, manifested as executive functions. Other cerebral cortex regions may also be assessed.

In certain embodiments, the anatomical region 10 that is studied is a forehead. Area 10 outlines the approximate region to measure an ion concentration and/or flux. In certain other embodiments, the region comprises a frontal, parietal, occipital, limbic, or temporal lobe of the individual. The spectroscopic device may also be used at more than one site on the individual. For example, depending upon the results at one site, the user may reposition the device to another cerebral region (generally 10), or another head or brain region (generally 10) altogether.

Figure 2:
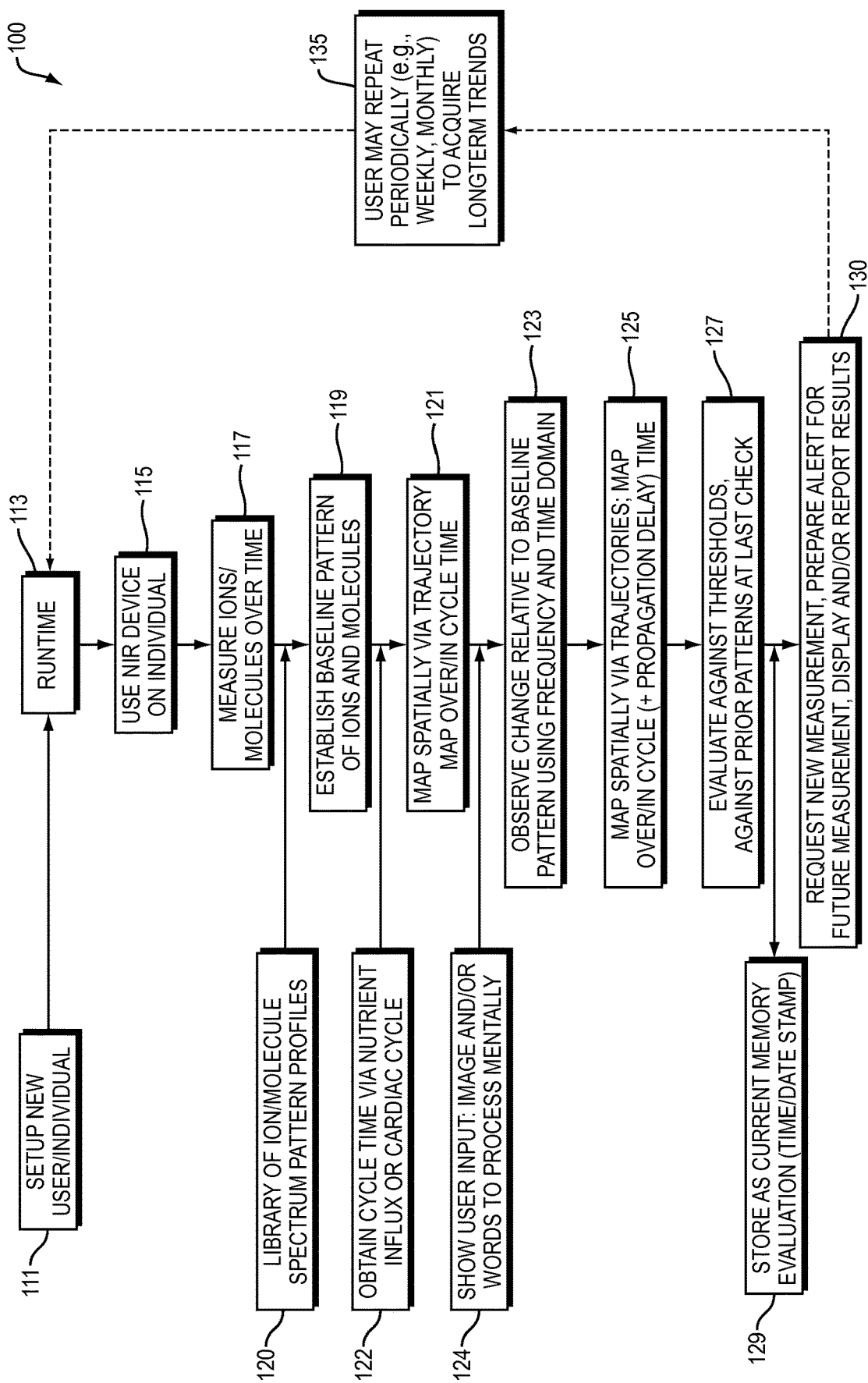
FIG. 2 is a flow diagram of one embodiment of the present invention.

As previously described in reference to FIG. 2, the method and system 100 include the determination of a measurement 117 of one or more ions, molecules, or combinations thereof. Such a measurement 117 is taken at two or more times (e.g., 2, 3, 4, 5, 6, 7, 8, 9, 10, 15, 20, 25, 30, 50, 100, etc.), and the measurements are compared 123, and this comparison enables the determination 127 of a probability for one or more neurons to generate an action potential. The ability of a neuron to generate an action potential increases the probability of forming a new memory.

In certain embodiments, the measured molecule is a nucleic acid, an amino acid, a sugar, a protein, a fatty acid, a nucleoside, a nucleotide, or combinations thereof.

In certain embodiments, the nucleic acid is a polymeric macromolecule or biological molecule. Nucleic acids include deoxyribonucleic acid, (DNA), ribonucleic acid (RNA), or artificial analogs of nucleic acids.

In certain embodiments, the amino acid is a naturally occurring amino acid or an artificial amino acid. Naturally occurring amino acids include essential amino acids histidine, isoleucine, leucine, lysine, methionine, phenylalanine, threonine, tryptophan and valine. Non-essential amino acids include alanine, arginine, asparagine, aspartic acid, cysteine, glutamic acid (or glutamate, the deprotonated form of glutamic acid), glutamine, glycine, ornithine, proline, selenocysteine, serine, and tyrosine. Amino acids can also include synthetic amino acids, or chemically derivatized amino acids, such as L-dihydroxyphenylalanine (L-DOPA). In certain embodiments, the amino acid is gamma-aminobutyric acid (GABA).

In certain embodiments, two or more amino acids are linked, forming a polypeptide that is measured. In some embodiments, the measured polypeptide is a protein. In certain embodiments, the protein that is measured is hemoglobin.

Sugars measured by embodiments include monosaccharides, disaccharides, and polysaccharides. Sugars can exist in linear chain or cyclic configurations, and include, but are not limited to glucose, sucrose, fructose, maltose, galactose, and lactose.

In certain embodiments, the fatty acid that is measured is a carboxylic acid having a long saturated or unsaturated aliphatic chain. Fatty acids include, but are not limited to, linoleic acid, alpha-linolenic acid, eicosapentaenoic acid, docosahexaenoic acid, oleic acid, elaidic acid, vaccenic acid, linoelaidic acid, arachidonic acid, erucic acid and so forth.

A nucleoside comprises a nucleobase (e.g. adenine, guanine, thymine, uracil, cytosine), bound to a 5-carbon sugar (e.g. a ribose or a deoxyribose in a pentose conformation), via a beta-glycosidic linkage. In example embodiments, the measured nucleoside is cytidine, uridine, adenosine, guanosine, thymidine or inosine, where the nucleoside contains either a ribose sugar component or a deoxyribose component.

In certain embodiments, a nucleotide comprises a nucleoside linked to one or more phosphate groups. In certain embodiments, the nucleotide that is measured comprises ATP, ADP, GTP, CTP and UTP, cGMP, cAMP, coenzyme A, FAD, FMN, NAD, or NADP+.

In certain embodiments, the measured ion is hydrogen ($H^+$), sodium ($Na^+$), potassium ($K^+$), calcium ($Ca^{2+}$), magnesium ($Mg^{2+}$), chloride ($Cl^-$), carbonate ($CO_3^-$), bicarbonate ($HCO_3$), or a phosphate ($H_3PO_4$, $H_2PO_4-$, $HPO_4^{2-}$, or $PO_4^{3-}$).

The ability of one or more neurons to generate an action potential is affected by conditions and parameters, as laid out in detail below, an assessment of which occurs in module 123. These conditions and parameters include: A. the concentration and flux of ions, B. acidosis, C. the concentration and flux of certain molecules, D. hypoxia, and E. cardiovascular parameters.

Returning to FIG. 2, the methods and apparatus 100 of the present invention also provide for the assessment at module 127 of hypoxia, acidosis, ion flux, or combinations thereof. Such an assessment is based on using the near infrared spectroscopic device 115 to determine one or more measurements 117 (including a baseline pattern 119) of one or more molecules, ions, or combinations thereof. Specifically, hypoxia is determined to be present based upon measured oxygen concentration ($PaO_2$), oxygen saturation ($O_2$ sat), arterial oxygen content ($CaO_2$), hemoglobin (Hb) concentration, or combinations thereof. A measured concentration of carbon dioxide ($CO_2$) can also be useful in the detection of chronic hypoxia because an elevated concentration of $CO_2$ would eventually not spur an increase in respiratory oxygen through to a sensed region of the brain (through the vasculature and the blood brain barrier to CSF at the brain stem). Oxygen in a healthy individual would increase quickly (within approximately 1-3 seconds), in response to an elevated concentration of $CO_2$, via increased respiratory action. Although it is possible that an elevated level of $CO_2$ could initially manifest at the exact time of testing in a healthy individual and before a corresponding rise in $O_2$, a detection of elevated $CO_2$ is more likely to indicate ineffective $O_2$ delivery and/or chronic hypoxia. Acidosis is determined to be present based upon measured concentration of hydrogen ($H^+$), bicarbonate ($HCO_3^-$), carbonic acid ($H_2CO_3$), $CO_2$, phosphates ($PO_4^{3-}$, $HPO_4^{2-}$, $H_2PO_4^-$, $H_3PO_4$), or combinations thereof.

As discussed above, persons with memory impairment suffer from a physiological inability or lowered ability to form new memories. A neurological memory is a process in which patterned input 124 is encoded, stored, and then later retrieved by an individual. Memories are formed and stored when neurons generate an action potential, for example a synaptic potential, or fire sufficiently above the action potential threshold, traversing from one presynaptic neuron to the next. Neurons manage electrochemical gradients such that reasonably small amounts of various ions can influence the cross-membrane potential. In an example embodiment, an appropriate action potential generates, and is followed by, a downstream recording event, or memory production.

Certain areas of the brain have been identified as being involved in memory, function, and storage, including the cerebral cortex, cerebellum, hippocampus, basal ganglia, amygdala, the striatum, and the mammillary bodies. Certain areas of the brain are thought to be involved in specific types of memory. For example, the hippocampus is believed to be involved in spatial learning and declarative learning, while the amygdala is thought to be involved in emotional memory.

There are several types of memories that are implemented by the brain in distinct ways. Working memory is the ability of the brain to maintain a temporary representation of information about a task that an animal or individual is currently engaged in. This sort of dynamic memory is thought to be mediated by the formation of cell assemblies or groups of activated neurons that maintain their activity by constantly stimulating one another.

Episodic memory is the ability to remember the details of specific events. This sort of memory can last for a lifetime. There is evidence that implicates the hippocampus in playing a crucial role in forming episodic memory. For instance, people with severe damage to the hippocampus sometimes have amnesia, the inability to form new long-lasting episodic memories.

Semantic memory is the ability to learn facts and relationships. This memory is probably stored largely in the cerebral cortex, mediated by changes in connections between cells that represent specific types of information.

There are many diseases, conditions, and other reasons that may cause memory impairment or loss, e.g., amnesia. Commonly, memory impairment or loss is associated with Alzheimer's disease. Other causes of memory loss or impairment may be from head trauma, drugs, alcohol, infections (e.g., encephalitis, HIV, Lyme disease), cardiovascular disorders (e.g., stroke, transient ischemic attack), psychological disorders (dementia, depression), neurological disorders (e.g., epilepsy, Parkinson's disease, Huntington's disease, multiple sclerosis), cancer (e.g., brain tumor), nutritional-deficiency (e.g., Vitamin B12), and aging.

For an individual suffering from memory loss, or the inability to form new memories, the study of certain chemicals in the brain can provide insight into the conditions underlying memory loss. As is detailed below, both Alzheimer's disease and conditions that cause an inability for neurons to form an action potential are, in certain embodiments, tracked or understood through analysis of particular ions and molecules.

Alzheimer's Disease and Brain pH:

Studies into Alzheimer's disease have examined the production of amyloid beta plaques and the role of amyloid beta plaques in the progression of Alzheimer's disease. Amyloid beta plaques are predominantly formed from mis-folded amyloid beta peptides. Particularly, the presence of a β-amyloid 42-residue peptide chain (Aβ42) indicates an Alzheimer's disease state due to its fibrillogenicity. Typically, β-amyloid 40-residue peptide chains predominate in healthy subjects. The occurrence of the β-amyloid 42-residue peptide chains is often a late-stage disease symptom.

Recent research has suggested that the soluble amyloid-beta oligomer (Aβ) disturbs synaptic function in earlier stages of the disease. Hippocampus research suggests that Aβ changes in memory (NMDA) receptors affect downstream $Ca^{2+}$ signaling pathways, such as calcineurin and long-term potentiation kinase CAMKII.

Research has also studied the amyloid precursor protein (APP), the protein that is cleaved by alpha-, beta-, and gamma-secretase to form amyloid peptide chains such as healthy Aβ40 or unhealthy Aβ42. Intermediate peptide fragments, for example C83 and C99, have been studied as well.

It is believed that beta-secretase (BACE1 enzyme) plays a pivotal role in the generation of Aβ42. Cleavage of APP by BACE1 generates peptide fragment C99, which is cleaved by gamma-secretase to form Aβ42. Consequently, BACE1 inhibitors have been considered as a potential treatment for Alzheimer's disease. BACE1 also has optimal activity under acidic conditions at around pH 4.5. Therefore, the generation of Aβ42 can be thought to proceed most efficiently when effective net [H+] is increased 100 or 1000-fold from biological pH. Alpha-secretase operates most efficiently at biological pH.

BACE1 is a transmembrane enzyme, whereas alpha-secretase is in membrane. The former activates when extracellular pH is lowered relative to normal intracellular pH.

In an example embodiment, in a person whose cardiac output has slowed, blood does not pump up and all the way through the cardiovascular system and into the far cerebral reaches of the brain. Without sufficient oxygenated-hemoglobin vascular delivery per every reasonably-timed cardiac cycle, the energy-producing adenosine triphosphate (ATP) cannot produce energy as well. Therefore, the extracellular solution increases in acidity with the higher $CO_2$ levels remaining present.

Extracellular acidity indicates that the fluidic concentration of positively-charged ions (cations) relative to negatively-charged ions (anions) has risen above biological range. Cells invoke working mechanisms including ion channels and pumps to try to restore homeostasis. However, cation:anion extracellular ratios that might shift by 100 or 1000-fold (pH of 4.6-6.0) relative to biological level impel cellular ionic influx/efflux, and happen to be outside the tighter range of electrochemical gradients that culminate in normal signals between neuronal cells.

When extracellular chemical gradients are then driven outside of their typical functioning ranges, the electrochemical gradients for sending and receiving signaling are then affected with varying probabilities depending on a number of factors, such as state, degree of pH disruption, and time to recovery.

Therefore, examination of extracellular acidity provides an indicator of BACE1 activity, thereby providing an early indicator of probability to form amyloid plaques later in an individual's brain.

Conditions that Affect the Formation and Propagation of an Action Potential:

Conditions in the intracellular and extracellular space have a profound impact on the ability of a neuron to generate an action potential. In certain embodiments, ion concentrations and flux, oxygen content, pH, the presence of other molecules, or combinations thereof can all impact action potentials.

A. Ions, Ion Flux, Ion Channels, Ion Transporters:

The ability for a neuron to generate an action potential and cause an input to be encoded and stored, for example, stored as a memory, depends in part on the intracellular and extracellular concentrations of certain ions.

In a normal (e.g., healthy) neural environment, potassium ions ($K^+$) contribute to the largest electrical component cross-membrane, but are less concentrated in the extracellular space than sodium ($Na^+$), chloride ($Cl^-$), and calcium ($Ca^{2+}$). See Table 1, below, for the extracellular and intracellular concentrations of different ions.

TABLE 1

Respective concentrations of the following ions and molecules
in extracellular and intracellular fluids for neurons at rest.

| Ion/Molecule | [Extracellular] (mM) | [Intracellular] (mM) |
| --- | --- | --- |
| $K^+$ (Potassium) | 0.003 | 100 |
| $Na^+$ (Sodium) | 140 | 10 |
| $Cl^-$ (Chloride) | 100 | 10 |
| $Ca^{2+}$ (Calcium) | 2 | 0.00005-0.0001 |
| $H^+$ (Hydrogen) | $4 \times 10^{-4}$ | $7 \times 10^{-5}$ |
| $Mg^{2+}$ (Magnesium) | 1-2 | 0.5 |
| $HCO_3^-$ | 21-29 | 8 |
| glutamate | 0.00002-0.03 | 1-100 |
| $HCO_3^-$ | 25 | 10-20 |

Potassium alone causes a cell to have a −80 mV resting potential, yet a neuron's membrane voltage adjusts slightly to around −73 mV due to the electrical contributions of $Na^+$ and other ions, intracellular protein anion contributions, relative ionic permeability, and combinations thereof. As calculated, the contribution of $K^+$ ions to effective mV could constitute ~91% in resting state.

At low pH, for example as in acidosis, the $Na^+/K^+$ pump operates to rectify the pH. However, since acidosis correlates with decrease in oxygen delivery, ATP production is affected. Therefore, the $Na^+/K^+$ pump, with decreased ATP available, is unable to maintain normal, physiologic extracellular and intracellular ion concentrations.

At this stage, ATP is no longer available to the cell to maintain healthy electrochemical gradients cross-membrane; the net movement of ions in the present electrical field due to chemical gradients and the osmotic movement of molecules through the cell's semipermeable membrane will start to spontaneously occur.

$K^+$ ions will efflux to rectify chemical imbalance between acidosis and hypoxia, while $Na^+$ ions influx. Other concentrations of ions also adjust. Without ATP energy delivery, the $Na^+/K^+$ concentrations would become effectively reversed. A neuron becomes depolarized, achieving, for example, a potential of about +73 mV, or more, the potential depending upon immobile residual intracellular protein, ions and combinations thereof. The membrane potential in certain embodiments is lower, as various ions influx and/or efflux, and and weaker forces start to dominate. For example, weaker forces include intermolecular forces such as dipole forces and Van der Waals forces.

When ATP production ceases, most ion pumps also cease. By contrast, Transient Receptor Potential Mediator 7 (TRPM7) activates current immediately when ATP is omitted. TRPM7 contains both an ion channel and a kinase domain, and selectively transports divalent cations such as $Ca^{2+}$ and magnesium ($Mg^{2+}$) among other metals. It is strongly activated when ATP decreases to less than 1 mMol.

Generally $Mg^{2+}$ is reported to inhibit TRPM7, but without available ATP, free $Mg^{2+}$ at biological concentration of 720 μM permeates the cell via influx. $Mg^{2+}$ current is greater than $Ca^{2+}$ through this channel.

TRPM7 is found in virtually every mammalian cell, although in different amounts. It is estimated that there are 10-100 channels per cell. The TRPM7 channel can serve to amplify excitatory postsynaptic potentials (EPSPs) through presynaptic vesicle release. The sum of individual EPSPs have a combined effect resulting in a larger EPSP, absent inhibitory neurotransmitters. The larger EPSPs result in greater membrane depolarization and increase the likelihood that the postsynaptic cell reaches the threshold for firing an action potential, necessary for encoding a memory. So far, larger EPSPSs seem only to be found in sympathetic neurons and at neuromuscular junctions where acetlycholine neurotransmitter is used.

B. Acidosis (pH)

pH can be considered as a measure of the acidity or basicity of an aqueous solution, with acidic solutions having a pH less than 7, and basic solutions having a pH greater than 7. The pH of blood is usually between 7.35 and 7.45, and is referred to herein as physiological pH or biological pH. However, the pH in other biological compartments can vary, e.g., the gastric acid in a stomach has a pH around 1 and pancreatic secretion has a pH around 8.

pH is defined as the decimal logarithm (base 10) of the reciprocal of the hydrogen ion ($H^+$) in a solution, written as:

$$pH=-\log_{10}[H^+].$$

pH also relates to acid/base relationships and electron donor/acceptor relationships.

Human neurons function in a relatively specific pH range of approximately 7.1 to 7.3 (Srinivasan, et al., pH-Dependent Amyloid and Protofibril Formation by the ABri Peptide of Familial British Dementia, Informa Healthcare, 11:1; 10-13 (2004), the relevant teachings of which are incorporated herein by reference in their entirety). An atypical shift in pH, for example, would cause neurons to immediately and automatically take measures to counteract the change, trying to restore the pH to biological pH levels in order to maintain function. For instance, astrocytes (astroglia) use a carbonate buffering system to manage extracellular pH.

A drop in pH, or acidosis, in the brain is undesirable, causing neuronal cells to alter their normal functioning in order to correct any such imbalance. Acidosis can arise regionally (locally) or encompass the entire brain (globally). Causes of acidosis include hemorrhage, arterial blockage leading to poor cerebral circulation, respiratory insufficiency or other factors, and acidosis can lead to stroke and/or death.

A neuron responds to its immediate environment, including the extracellular space. The extracellular space is less voluminous relative to the volume and size of a neuron (made up of axon, dendrites, soma etc.). A regional change (e.g., in pH) can affect one or just a few neurons. Even more localized changes (e.g., in pH) may only affect a single dendrite or a side of an axon.

The methods and apparatus described herein include assessing pH changes in the brain. These changes may be regional or global pH changes. As described above, the pH changes may involve a single neuron, or multiple or a group of neurons. Determining where acidosis is occurring in the brain can aid in determining or predicting a likelihood of memory impairment in an individual. The system modules/steps 117, 119, 121, 122, 123, and 125 (FIG. 2) provide for tracking, monitoring, and mapping pH values over time.

Furthermore, as discussed above, the activity of BACE1 is optimized under acidic conditions of about pH=4.5. With increasing BACE1 activity, the probability of later amyloid plaque formation is increased.

C. Presence and Concentration of Molecules: Neurotransmitters, Drugs, Other Chemicals As described herein, an array of molecules and ions are measured 117 to afford this insight into memory formation. For example, the molecules and ions can include neurotransmitters, drugs, chemicals, receptors, and so forth. In an example embodiment, N-methyl-D-aspartate (NMDA) receptor is measured. NMDA is involved in controlling memory and learning. In order to map an action potential, both ligand-ion-channel and voltage gating must take place simultaneously.

In certain embodiments, a magnesium ion is measured at 117. An $Mg^{2+}$ ion blocks the receptor channel in a voltage-dependent manner. Current state-of-the-art states that it is rolled away when the cell depolarizes.

In certain other embodiments, ATP is measured at 117. Without ATP, cross-membrane flux between resting potential and +50 mV or more depolarization may be occurring. The TRPM7 channel can be activated and removes $Mg^{2+}$ blockage of NMDA receptor. Without ATP, the glutamate transporter direction depends upon the ion gradient. Glutamate can be released instead of removed from the synapse.

According to embodiments, voltage may also be calculated according to the equation:

$$\text{Effective voltage} = A \sin(\omega t + \Phi)$$

where A is amplitude, $\omega$ is angular frequency ($\omega=2\pi f$; where f is frequency), t is time, and $\Phi$ is phase.

D. Hypoxia ($O_2$):

Periods of hypoxia cause depolarization of neuronal membrane, which ultimately ceases the action potential discharge, or firing activity, of the neurons. While brief periods of hypoxia can cause reversible depolarization of the neuronal membrane, longer periods of hypoxia contribute to irreversible depolarization (Calabresi, P., et al., On the mechanisms underlying hypoxia-induced membrane depolarization in striatal neurons, Brain, 118 (Pt 4):1027-38 (1995), the relevant teachings of which are incorporated herein by reference in their entirety).

Figure 3:
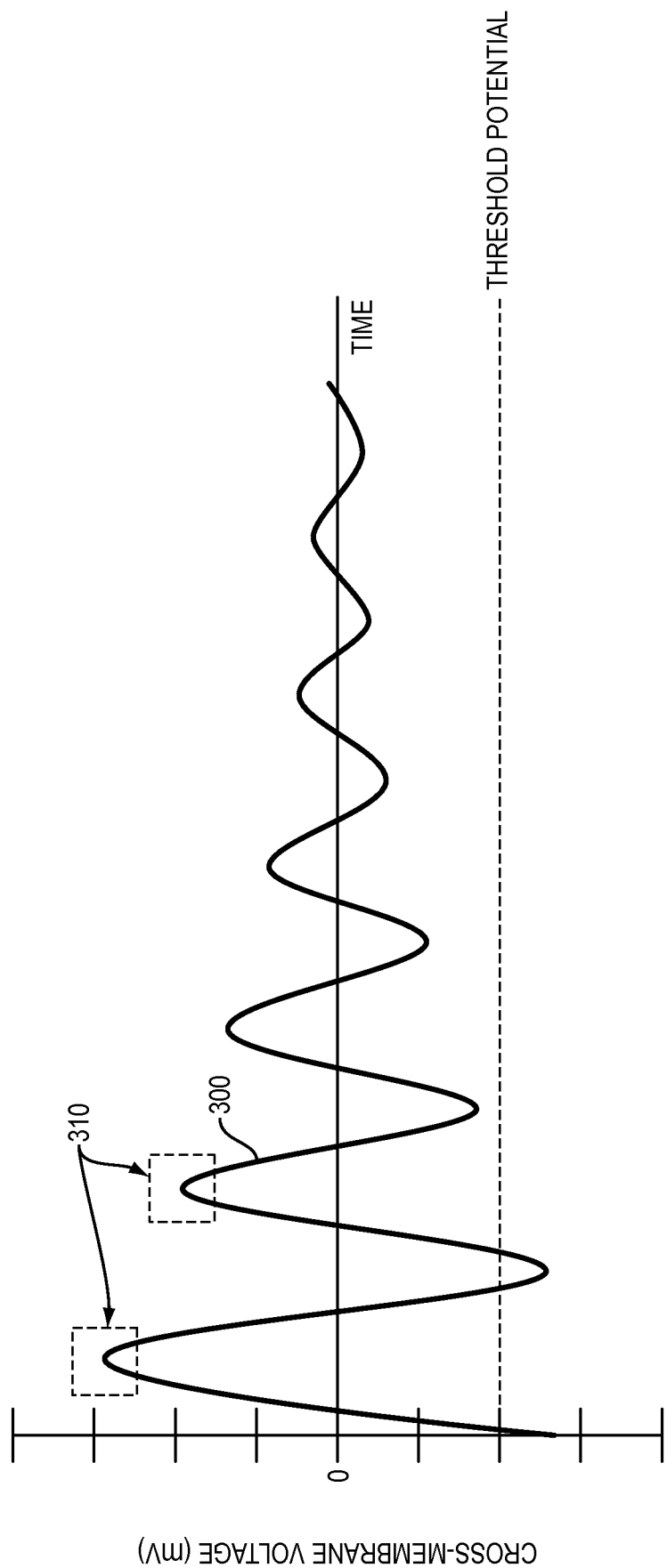
FIG. 3 is a graphical representation of a theoretically isolated neuron's possible electrical gradient over time in the presence of acidosis and/or hypoxia.

As illustrated in the graph of FIG. 3, a theoretically isolated neuron has an attenuating electrical gradient 300 over time in the presence of acidosis and/or hypoxia. Other curves are possible, for example where the decay rate, angular frequency, phase, amplitude and/or recovery time window is varied. The graph is similar to a damped sine wave, which is a sinusoidal function whose amplitude 310 approaches zero as time increases. When ATP becomes no longer available to power the cell's maintenance of gradients at start time on the graph, for example, the cell (neuron) might happen to be in its resting phase or approximately –70 mV (millivolts).

E. Cardiovascular Effects (Bloodflow, Blood Pressure, etc.)

Blood carries and transfers nutrients through the epithelial cell barrier that lines cerebral microvessels (commonly called "blood-brain barrier"). Nutrients in blood such as bicarbonate, $K^+$, $Na^+$, and water transport through the blood-brain barrier to the circulating extracellular fluid (ECF). Interstitial fluid (ISF), although cyclically-slower than blood flow, bathes the surrounding neurons. Interstitial or extracellular spaces are tight and can be further congested with extracellular networks, other cells and transmembrane protuberances. Due to these reasons, ion concentrations may sometimes vary by locale.

The effective transfer of nutrients and ions from each fluid compartment to the next effectively diminishes. The movement of ions and nutrients slows from the blood to the ECF or ISF proximate to the neuron sublocale where needed. Via water flux and osmolarity, blood flow and pressure become the driving force for CSF formation (by the choroid plexus epithelial cells) and nutrient transmission, to enable the cell's electrical duties and to power sufficient gradients above action threshold when needed.

Memory Evaluation

As described herein, embodiments of the invention relate to a tool 100 (FIG. 2) that recognizes any such "real-time" acidosis and/or hypoxia. As will be apparent to one of skill in the art, the methods and apparatus described herein can be useful in cases of hypoxia, diabetes, cerebral infarction, arterial stenosis, decline in cardiac output, insufficient $O_2$ delivery performance from oxygenated-hemoglobin, or periods of postural stasis that exacerbates low rates of oxygen unloading or waste removal.

In certain embodiments, the methods and apparatus 100 further include establishing a baseline 119 from the first measurement of each of the one or more ions, molecules, or combinations thereof at the first time, and utilizing a library of ion/molecule spectrum pattern profiles 120. That baseline measurement 119 provides a memory map 121 of the individual. As used herein, "memory map" refers to a correspondence duality defined between memory and spatial regions. In some ways, a memory map is similar to a highway or road map, where a memory map represents an individual's aspects of memory against his brain regions. A memory map 121 can also contain information regarding a hierarchy in memory strengths and memory weaknesses, types of memory processed, anatomical delineations, branching, density of storage, etc. In certain embodiments, the memory map 121 is normalized based on gender, age, diet, height, weight, medical history, race, environmental factors, genetic dispositions, athletic level or ability, cardiovascular profile, or other physical, mental, social, or any other characteristic of the individual. A memory map can be represented at high-level (regional) or low-level (molecular, ion) detail.

Another embodiment of the invention is directed to a computer system 100 to predict a likelihood for memory impairment in an individual. The computer system comprises a measuring module 117 (FIG. 2) configured to determine a first measurement of each of one or more ions, one or more molecules, or combinations thereof at a first time and configured to determine a second measurement of each of the one or more ions, one or more molecules, or combinations thereof at a second time (subsequent to the first time). The computer system 100 further comprises a comparison module 123 configured to compare the first measurement to the second measurement of each of the one or more ions, one or more molecules or combinations thereof. The comparison module can provide an updated memory map 125 including information regarding propagation delay. The computer system 100 further comprises a probability module 127 coupled to the comparison module 123 and configured to determine a probability for one or more neurons to generate an action potential, wherein the generation of an action potential increases the probability of forming a new memory. In that way, probability module 127 predicts the likelihood for memory impairment in the individual (forms such a prediction based on determined probability) by evaluating changes against thresholds and prior patterns.

In a preferred embodiment, memory maps 121, 125 can be low-level memory maps, representing specific spatial trajectories. Memory map 129 can be a high-level memory map, permitting users to see a simplified, regional view. Memory maps 121, 125, 129 can include and represent data in a three-dimensional manner.

In certain embodiments, the computer system 100 further comprises a baseline module 119 configured to establish a baseline from one or more measurements of the one or more ions, molecules, or combinations thereof at the first time. That baseline measurement 119 provides a memory map 121 of the individual, as described above. In further embodiments, the computer system 100 also comprises a normalization module configured to normalize the memory map 121 based on gender, age, diet, height, weight, medical history, race, environmental factors, genetic dispositions, athletic level or ability, cardiovascular profile, or other physical, mental, social, or other characteristics of the individual. In some embodiments the measuring module 117 includes a baseline submodule and/or normalization submodule.

The present invention also provides for the computer system to further comprise an assessment module 127 configured to assess hypoxia, acidosis, ion flux, or combinations thereof. When hypoxia or acidosis is present or when ion flux is accordingly increased or decreased, the likelihood for memory impairment is increased. In some embodiments the comparison module 123 and/or probability module 127 is referred to as an assessment module.

In certain embodiments, the computer system 100 further comprises a second measuring module configured to measure cerebral blood pressure, cerebral blood flow, or combinations thereof. In some embodiments the measuring module 117 is further configured to measure cerebral blood pressure, cerebral blood flow, or combinations thereof. Measurements of cerebral blood pressure and cerebral blood flow can provide useful context for other measurements, such as ion flux.

The present invention provides for the computer system to further comprise a device module 115 configured to connect one or more infrared spectroscopic devices 115, 50. In some embodiments, the device module 115 is operatively part of the measuring module 117.

In certain embodiments, the present invention enables the discovery of new regions of memory loss. In alternate embodiments, the invention identifies new regions of memory loss with high probability. For example, the invention can produce a visual image depicting concentration and migration of a target ion, for example $Mg^{2+}$ or $K^+$. In a further embodiment, an assessment of the total effective ion gradient is produced by steps/modules 119-125, which can suggest (by module/step 127) whether the gradient is fluctuating sufficiently to generate a threshold action potential value.

System 100 also allows for flagging or sending an alert 130 if a region is designated (or determined) to have or to potentially have memory loss. Such an alert can also indicate the locale of the region at risk. The alert is sent (by module/step 130) to the individual, the individual's designated devices or wearable aids, a member of the individual's family, an individual's health proxy, a healthcare provider, one or more persons designated by the individual, or a combination thereof. In certain embodiments, the computer apparatus/system 100 at 130 automatically triggers an alert, for example as an email, a banner, or other electronic communication, to be sent to the designated recipient. In another embodiment, the report/alert module 130 correlates future risk of memory loss in a region against threshold action potential. Report/alert module 130 can also provide an alert to the user to obtain a future measurement and can also report out the results to the user or a third party. The user may repeat the process (steps 115-130) repeatedly over time to acquire long-term trends, as shown in step 135.

In certain embodiments, the present invention enables the discovery of existing pockets of previously lost neurons, or lost memory. In an example embodiment, module/step 127 identifies such regions through tracking ion flow; any regions of relative ion flow trajectory silence can be indicators of previous neuronal apoptosis or necrosis, or can indicate glial cleanup.

Ion and molecule concentration are useful to assess because these are signaling enablers that correlate to healthy range of memory function. Furthermore, in regions having a low pH, potassium or calcium can be the largest contributor to wrong signaling scenarios.

New regions of memory loss and existing regions of previously lost neurons can be discovered and assessed based on a number of measureable parameters. In certain embodiments, these measureable parameters include the effective rate of oxygen unloading, measured, for example as oxygen concentration per unit time or per cardiac cycle at 122. In another embodiment, oxygenated hemoglobin concentration ([HbO]) per unit time or per cardiac cycle is measured at 122. In another embodiment, the measureable parameter includes rate of ATP production. In another embodiment, hydrogen ion concentration is measured per unit time or per cardiac cycle at 122.

In the above embodiments, if the concentration is below some previously indicated threshold, an alert or flag is raised, as described in the methods (report/alert module 130) above. The previously indicated threshold in module 127 can be designated by the computer application/system 100, by the individual, by the user, by a health care professional and the like.

In alternate embodiments, pH is detected, or alternately determined from the measurements of ion concentrations 117 or from bicarbonate buffering system measurements (e.g. bicarbonate, carbonic acid). In certain embodiments, pH detection provides an evaluation of signal strength, memory retention, memory recall, depth of neuron branching, and energy storage via capacitance (e.g. delta charge, charge state).

In certain embodiments, as illustrated at step 124 in FIG. 2, an input image is supplied to a user. Through the input image, the computer system/apparatus 100 (modules 117-129) or the user can track ionic flux, trajectories of ions, lack of ions or target molecules in a particular subregions, changes in pH, hypoxia or ischemia, or other information.

The invention displays on screen and/or provides a report in which the likelihood for memory loss is reported or otherwise output 130 to the individual or user. As discussed above, the display/report optionally comprises a comparison against memory impairment observed in other individuals, or alternately provides a spectrum on which an individual's memory impairment is ranked. Such a comparison, or such a spectrum, can include an analysis of age, education level, physical fitness, or other characteristics of an individual. In other embodiments, memory impairment is compared to or assessed against another measurement or prediction of memory impairment of the same individual, taken at an earlier time period (date), for example, five years prior.

Circulatory Evaluation

The frequency and volume of pulsations of blood through the vessels of the brain are directly related to the oxygenation of, and nutrient delivery to, brain tissue. Therefore, in order to assess the function of an individual's brain circulation, embodiments of the present invention provide methods and apparatus for measuring the frequency and volume of blood pulsations or flow through brain vessels and methods for analyzing such information in order to obtain functional features of the individual's brain circulation. Both arterial and venous vasculature can be captured and measured. Additional information pertaining to an individual's cerebrospinal fluid flow may also be measured and presented.

Utilizing a mobile device equipped with a camera, a user of the device can capture a series of images of the individual's face, head, and neck regions. The user of the device can be the individual. A camera capturing images in the RGB (red-green-blue) spectrum of visible light provides information on the vascular pulsing and progression of blood through blood vessels travelling beneath the subject's skin. A camera capturing images in the near-infrared spectrum captures similar information of the vasculature contained beneath the skull of the individual. By capturing a sequence of images over a period of time, frequency and volume of blood pulsations and flow are measured. Such pulsation and flow information is reconstructed and graphically represented to the user through an animated and touch-sensitive user interface. In one embodiment, the graphical representation includes a map of the individual's vasculature. In another embodiment, a generic representation of the vasculature of the brain and face of a human is displayed, with subject-customized pulsation animation superimposed onto the generic graphics. Various representations of blood and/or nutrient transport to the brain can be depicted, in addition to other information, such as the flow of cerebrospinal fluid.

Figure 4:
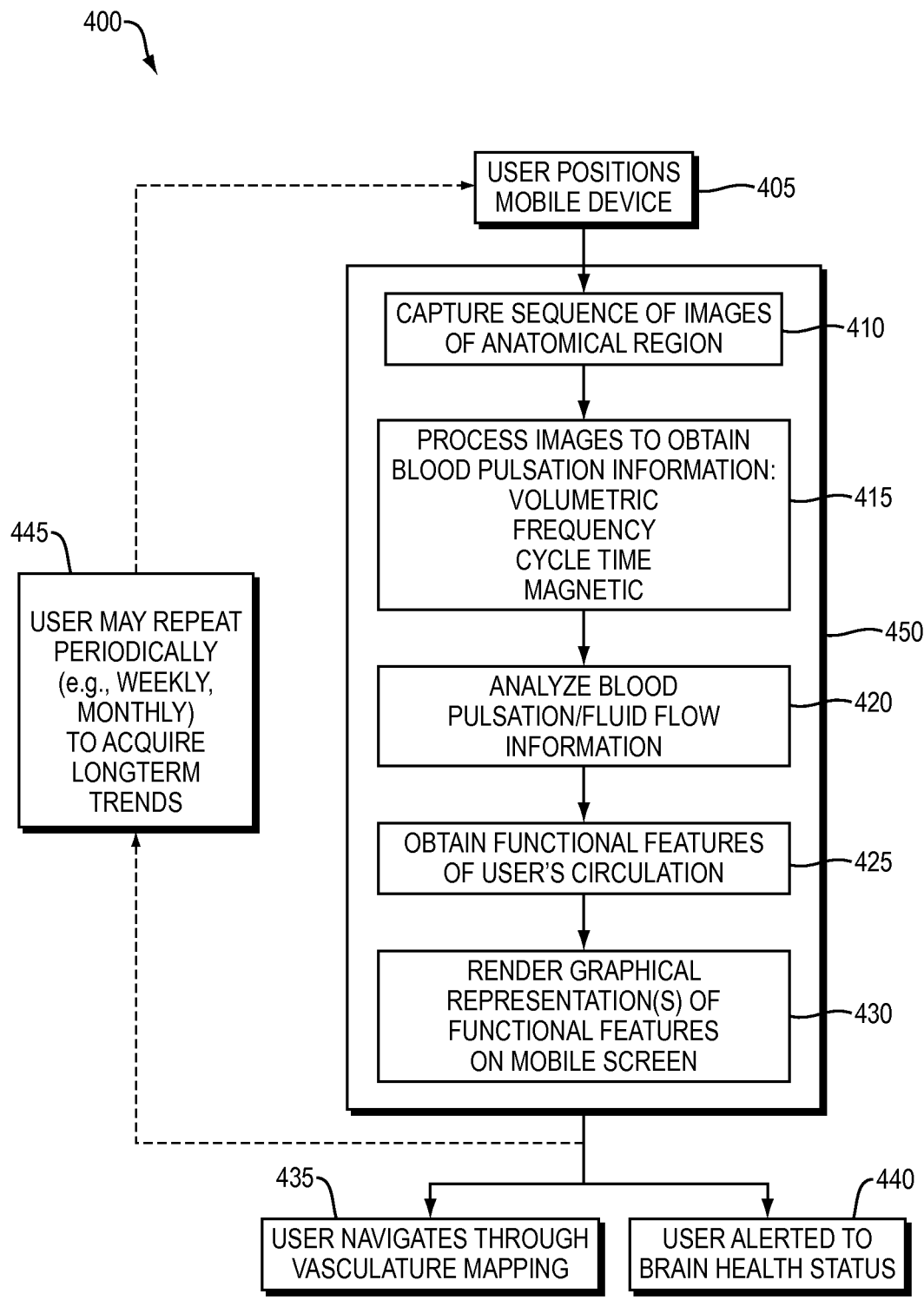
FIG. 4 is a flow diagram of one embodiment of the present invention.

Accordingly, embodiments of the invention are directed to a method, system and apparatus for capturing and presenting circulatory information relating to the pulsation and flow of fluid, including blood and CSF, within an anatomical region of an individual. An embodiment 400, illustrated in FIG. 4, includes positioning a mobile device (step 405) having at least one camera equipped to capture photographs in the RGB and near-infrared spectrum in front of the face, head, and/or neck of the individual, e.g. the user. The mobile device captures a sequence of images of an anatomical region of the user, as shown in step 410. The circulatory information provides information relating to volumetric, frequency, cycle time and magnetic behavior (step 415), including, for example, changes in the volume of a vessel, changes in the frequency of blood pulsations through an artery, and changes in the flow of fluid through a vein or sinus cavity. This information is analyzed (step 420) to produce functional features of the user's circulation (step 425), which is rendered graphically on a screen of the device for user viewing (step 430). Graphical rendering (step 430) can include and represent data in a three-dimensional manner. The user is then able to navigate through a mapping of the user's vasculature while viewing real-time information relating to volumetric, frequency, cycle time and magnetic behavior (step 435). Additionally, the user can be alerted to brain health status, including any potentially negative markers of brain health (step 440). The user may repeatedly capture images to acquire long-term trends (step 445), in which case the mobile device captures additional data points and the user can be provided with additional and historical data relating to the user's brain health.

Figure 5A:
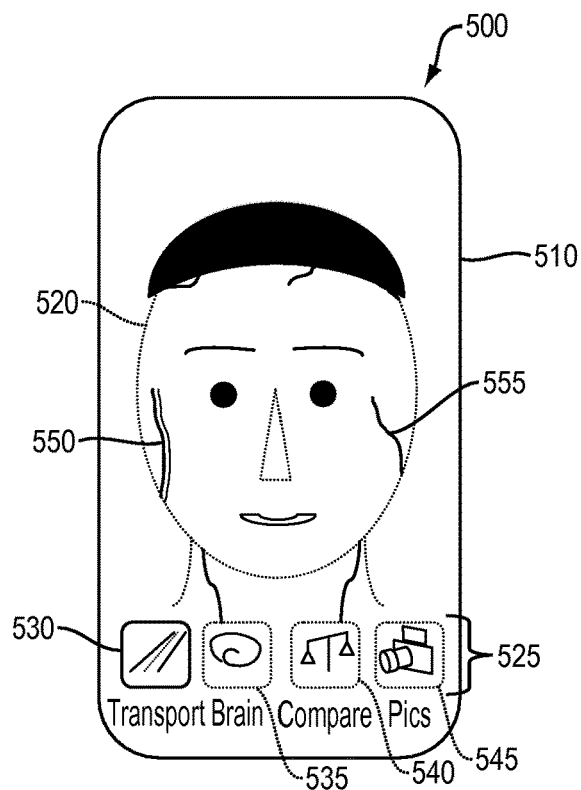
FIGS. 5A-5E are schematic illustrations of a user interface for visualizing and manipulating brain, face, and neck circulatory information.

FIGS. 5A-5E schematically illustrate a user interface 500 for visualizing and manipulating brain circulatory information. FIG. 5A illustrates the region(s) captured by the camera of the subject 520 and depicted on a display 510 of the device screen, along with user-selectable viewing modes 525, including "Transport" mode 530, "Brain" mode 535, "Compare" mode 540, and "Pics" mode 545. Vasculature 550, 555 of the subject can be made visible, either through generic representations of vessels or through a reconstruction of the subject's own vasculature following imaging. In FIG. 5A, the Transport 530 viewing mode is shown to be selected and highlighted, representing the circulatory function of the subject's brain, head, and neck. Other viewing modes 525 are shown dimmed. The vasculature 555 of the subject 520 can be displayed with a precise line to indicate an oxygenated vessel, or a vessel for which an adequate amount of imaging data has been captured. Vasculature 550 can be displayed with a dimmed or less precise line to indicate a less-oxygenated vessel, or to serve as a default representation until an adequate amount of imaging data has been captured.

Figure 5B:
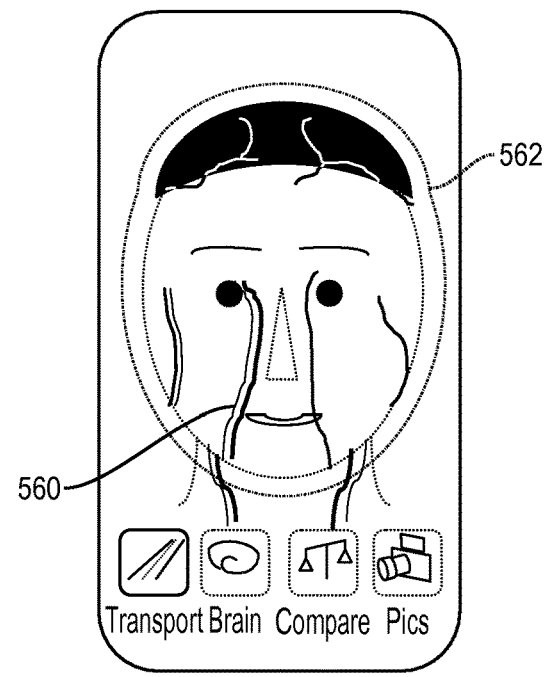

As the camera continues to capture imaging data in the RGB and near-infrared spectrums, additional vasculature 560 may populate on the display 510, as shown in FIG. 5B. The depicted vasculature can pulsate to indicate an active artery, or in correspondence with the subject's pulse. Audio tones or vibrations may pulse synchronously as well. A compendium of fluidic pulsations which cyclically expand the cranial space can appear with a pulsing surround 562. Some facial and skull bones, particularly finer bones, articulate in order to accommodate pulsational flow. Such articulation can have a lateral average of about 2 mm, which can be detected by dynamic sequencing of images.

Figure 5C:
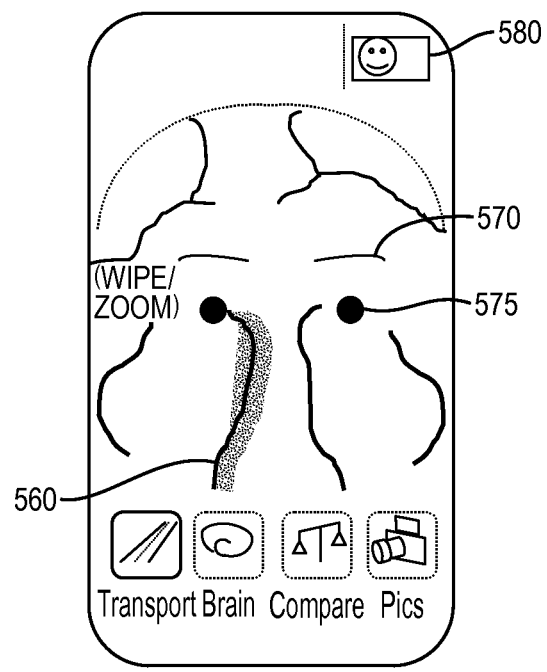

As additional detail regarding the vasculature is captured and displayed, facial features may recede from view and zooming may occur, as depicted in FIG. 5C. Vasculature 560 can be displayed with a blurring effect as a means to display relative motion of the vessel. For example, edges may be represented with a lighter, blurred effect to represent areas where a vessel wall spends less proportional time, while a central area are of the vessel can be represented with a darker, solid effect. Volume changes in the vessel can be imputed from the detected pulsations. Additionally, a rate of volume change over time can be calculated. Some facial features, such as eyebrows 570 and eyes 575 can remain for the user to maintain a sense of orientation. In addition, or alternatively, an icon 580 can be displayed depicting a face to indicate the present view, or stage within the Transport mode, to the user. Additionally, continuity between the RGB and near-infrared images can be achieved by using features such as eyebrows 570 and eyes 575 as markers. Vasculature behind the skull, captured with the near-infrared camera, and vasculature behind soft tissue, captured with the RGB camera, must be aligned both spatially and cyclically to provide for oxyhemoglobin correspondence and delay, as well as for visualization purposes.

Figure 5D:
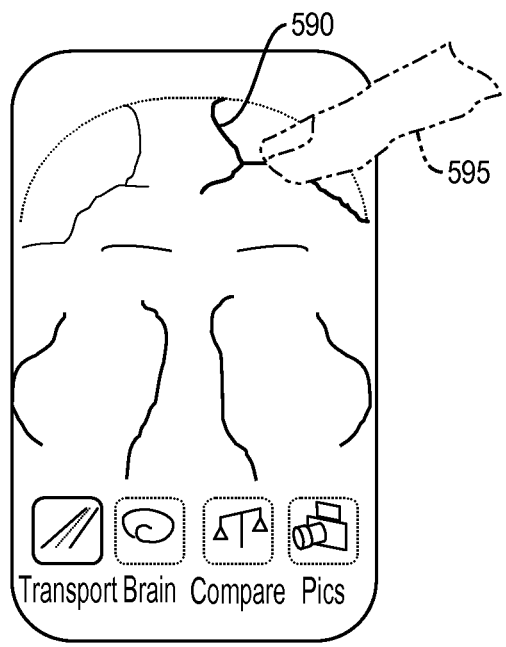

As shown in FIG. 5D, cardiovascular network regions can be touch-sensitive and, upon selection by the user 595, the display 510 may responsively highlight a selected vessel 590 and provide the user with a further zoom view or additional information regarding the selected vessel. If the viewing camera has shifted during the active capturing of images of the subject's anatomy, a re-view may be suggested to the user, or prior cycle data previously captured may be substituted.

Figure 5E:
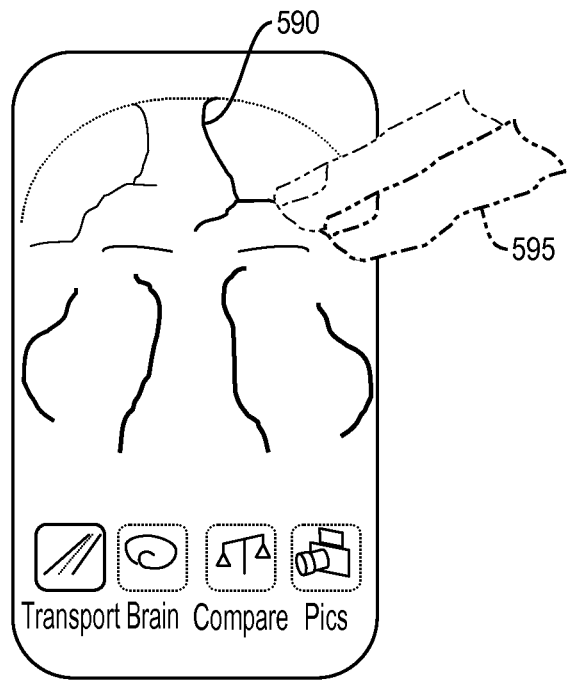
Figure 6A:
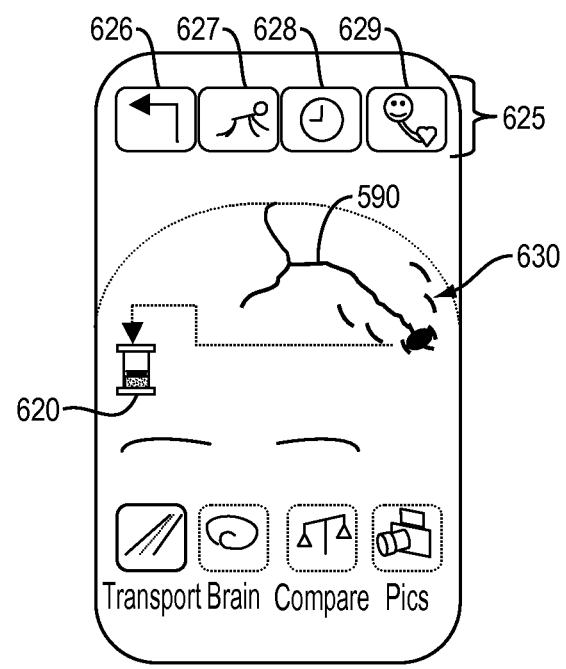
FIGS. 6A-6C are schematic illustrations of a user interface for further visualizing and manipulating captured brain circulation information.
Figure 6B:
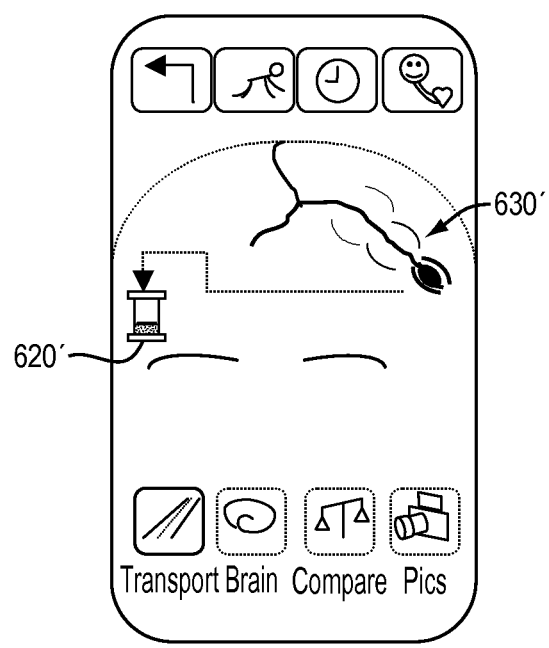
Figure 6C:
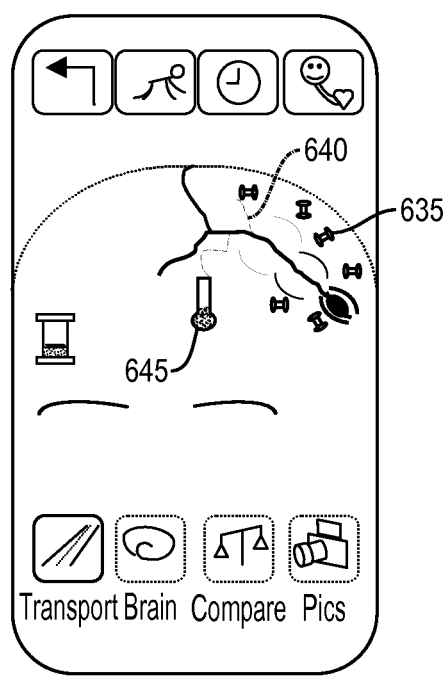

As shown in FIG. 5E, cardiovascular network regions may be swipe-sensitive, and upon selection by the user 595, the next Transport stage may be invoked. As shown in FIG. 5E, a user swipes along a vessel of interest 590. The next Transport stage then appears, as further described with respect to FIGS. 6A-6C FIGS. 6A-6C schematically illustrate a user interface for further visualizing and manipulating captured brain circulation information, which includes additional, user-selectable options 625. FIG. 6A illustrates additional information pertaining to a user-selected vessel 590, including a representation of real-time pulsing of the vessel 590. The animation of the real-time progressing wavefronts 630 represents the pressure, displacement, and/or energy density waves propagating from the blood vessel over time. Pulse wavefronts refer to the forward edge of a contiguous fluidic mass. For example, a progressing, continuous train of transverse wavefronts 630 can be shown, the transverse wavefronts spatially evolving through the blood vessel wall and/or through surrounding tissue fluid over each pulse cycle. The spatial evolution of progressing transverse wavefronts can be represented to spread and decay via outward motion from the vessel. Pulse wavetrains, referring to more than one contiguous fluidic mass, briefly expand a vessel wall during the transit of blood, and the expansion pushes into extracellular fluid (ECF) and cells. This expansion transports energy into the surrounding fluid and relates to the delivery of nutrients which cross the blood-brain barrier. An indicator 620, such as a battery, can represent to the user in a visually and easily-comprehensible manner the assessed energy delivery of the pulse wavetrains propagating from a vessel wall. Additional options 625 can include a crawling feature 627 which permits the user to see a slow-motion view of the pulse wavetrains at, for example, half or quarter speeds, so that the user can better see the inter-relationship between pulse and energy delivery. Additional options 625 can also include selections for a go-back option 626, a freeze-frame option 628, and an option for viewing disparate aspects of the cardiovascular cycle together 629. Other variables, such as the radial torqueing force of blood against a vessel wall can also be changed in a "what-if" function by the user.

In comparison with FIG. 6A, FIG. 6B schematically illustrates the display of a subject having reduced pulse wavefronts 630', representing poorer brain circulatory function. For example, the pulse wavefront 630' is smaller in amplitude and spreads more slowly over time. An indicator 620', such as a battery, can also represent to the user reduced energy delivery.

Additional representations of circulation are shown in FIG. 6C with oxygen barbells 635 representing sufficient oxygen delivery. The oxygen barbells 635 can bob with represented wavefronts. Additionally, several capillaries 640 are shown to demonstrate a location at which oxygen gas molecules are actually unloaded, as opposed to their traveling origins as plasma and each HbO molecule is propelled through the vessel. All vessels pulse, however capillaries pulse irregularly. In health, $O_2$ oxygen delivery is relative to $O_2$ oxygen concentration in proximate extracellular fluid and tissue, beyond capillary delivery of oxygen. Oxygen concentration in surrounding fluid and/or tissue may be calculated by pH, or by aerobic versus anaerobic pathway assessments. An oxygen level indicator 645 can be displayed, which can further represent the overall sufficiency of oxygen delivery to a regional area near the selected blood vessel. For some users, it may be important to show both deoxygenated hemoglobin and oxygenated hemoglobin in cycle time.

Figure 7A:
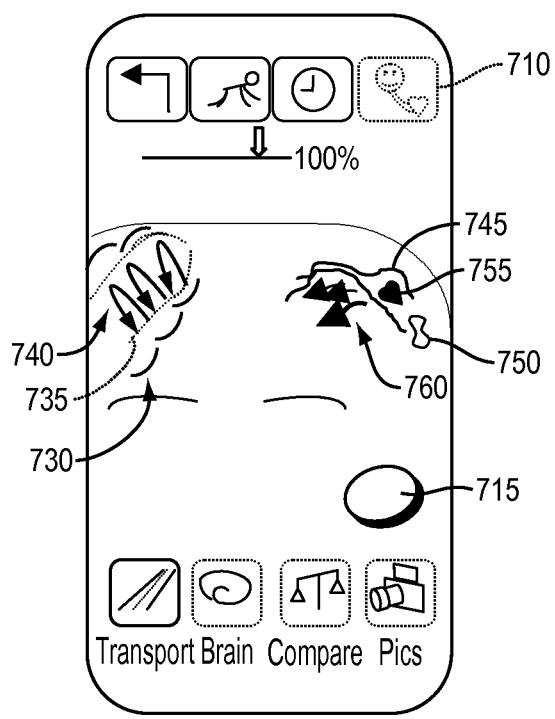
FIGS. 7A-7B are schematic illustrations of another user interface in which related but disparate anatomy are represented in the same display.
Figure 7B:
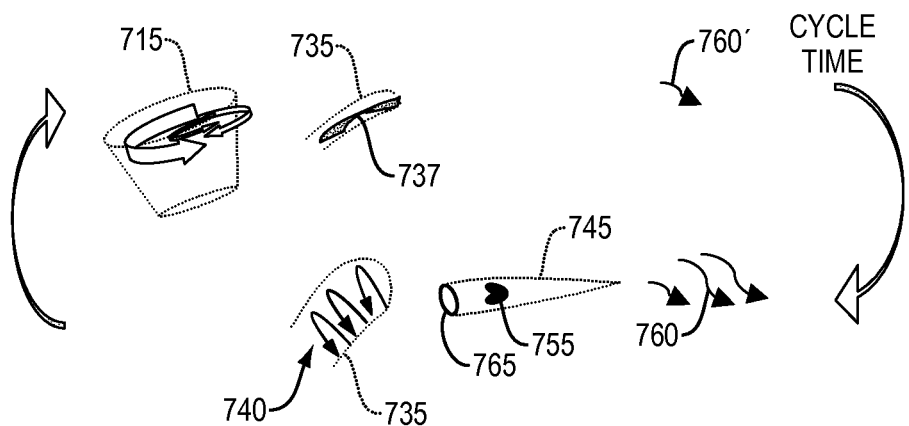

FIGS. 7A-7B schematically illustrate a user interface in which related but disparate anatomy are represented in the same display. Option 710 is shown to be selected, which represents to the user that features of the face and heart are shown together on the display screen. Heart 715 is animated to pulse based upon real-time information acquired from the subject or upon prior cycle data obtained from the subject. Additionally, an artery 735 and a capillary 745 are shown and display animated representations of pulse wavefronts 730 and nutrient delivery arrows 760. Pulse wavefronts 740 represent the blood rotationally spinning in a spiral within artery 735. A deformed red blood cell 755 is depicted squeezing through the capillary 745 with its embedded oxygen (HbO) yet to be drawn down. A spent red blood cell 750 having a typical biconcave shape is depicted, shown to be relatively depleted of oxygen due to earlier $O_2$ gradient drawdown in the tissue by which the red blood cell 750 passed. This user interface provides educational information, showing ejection from the heart and nutrient delivery in the brain on the same screen. The heart, artery, and capillary can be animated to correspond to each other in real-time. For example, the pulsations of the heart precede the pulse wavefronts 730 of the artery 735.

Touch actions within the user interface can allow the user to see how his or her nutrient-in and waste-out systems relate and depend upon each other. FIG. 7B depicts some cardiovascular components and downstream components in abstract. During a first phase, a heart 715 is initially shown in systole, during which time, less blood 737 remains in the vessel 735 and nutrient delivery arrows 760' are shown to be at a minimum. During a second phase following systole, and after a period of time where blood has reached the capillaries, nutrient delivery arrows 760 are shown to increase. Additionally, a representation of a red blood cell 755 is shown to travel through a capillary 745, with a precapillary sphincter 765 in an open position. During the period of time after a subject's mitral valve closes, but before the aortic valve opens, concentric layers of blood can progressively counter-spin in a conductive pattern with the rotational compression of blood inducing contraction of the ventricle. The first phase, showing the heart 715, vessel 735 and nutrient delivery 760' in cyclic correspondence, shows the user that, during systole, a vessel has less blood, which is travelling at a slow rotational/forward pace, as a pulse wavefront has not yet occurred. The second phase shows cyclic correspondence of the vessel 735, capillaries 745, and nutrient delivery 760 during a pulse wavefront. Arrows 740 represent the rotational layers of spinning blood in the vessel 735. More rotations of blood relate to more energy delivered. The heart and vasculature inter-animate at one time, to demonstrate their relation and dependence on one another.

Touch actions can be available from the objects representing the heart and vasculature. Examples of user input and corresponding results are provided in Table 2.

TABLE 2

Touch actions by user and examples of corresponding displays.

| User Action | Pinch Parallel to vessel axis | Expand/Pinch Normal to vessel axis | Double Tap Precapillary sphincter | Swipe Axial to nutrient flow | Expand/Pinch Through tissue |
|---|---|---|---|---|---|
| Response | Show "squeezing" of vessel so less fluid can get through at a time, depicting slower velocity of fluid | Next class of vessel (Vessel classes: artery, arteriole, capillary, venule, and vein) | Show +5% tissue oxygen usage, pcapO2 and RBCs in | Show next stage: Co2 efflux | Increase "wash out" animation of nutrients as they are utilized/ therefore increase diffusion rate |

Figure 8A:
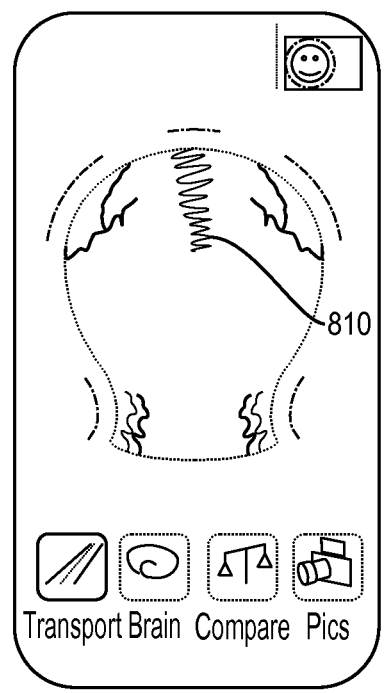
FIGS. 8A-8C are schematic illustrations of user interfaces for displaying the transport of venous outflow and cerebrospinal fluid.
Figure 8B:
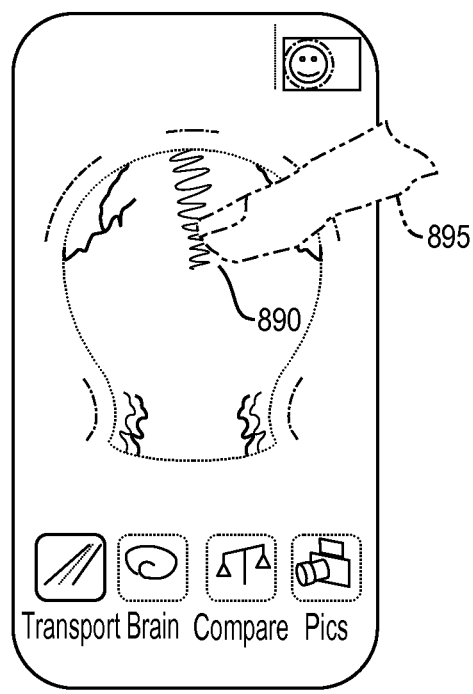
Figure 8C:
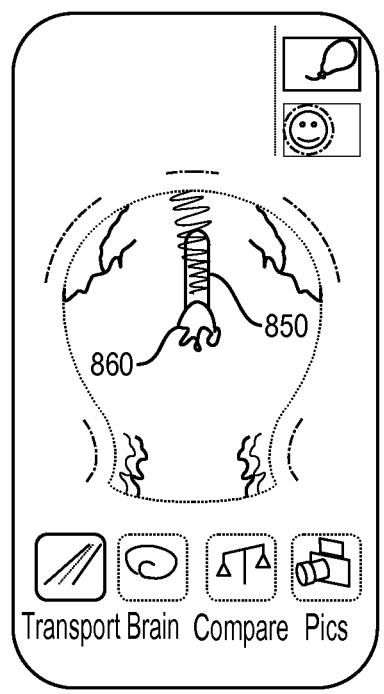

User interfaces for displaying transport aspects of venous and cerebrospinal fluid are shown in FIGS. 8A-8C. By selecting the pulsing surround 562 (FIG. 5B), the user may invoke displays and animations pertaining to these other fluid compartments of the brain: venous and CSF. CSF flow is fundamental to nourishing brain tissue and removing toxic metabolic wastes. Together with blood flow supplying the cerebral brain, CSF flow contributes to intracranial pressure (ICP). CSF flow is subject to cycling gradients of pressures, as described above with respect to blood flow through vessels. Elevated intracranial pressure can lead to increased cerebral perfusion pressure (CPP) and impaired filtration from brain tissue and impaired nutrient uptake. Such impaired function could lead to stroke, or could ensue as hydrocephalus. Ageing, head injury and other factors can elevate ICP.

Because brain tissue is generally soft and pliable, in order to metabolically absorb nutrients and eliminate waste via surrounding flow, cerebral CSF flow and ICP are important factors. CSF's slow, rhythmic flow pulsations help cause rippling of O2 gas and molecules/ions towards tissue, and cause harmful byproducts, such as CO2 gas, lactic acid, and acetic acid, to move away. Although daily CSF production contributes to ICP, in healthy individuals, the more rapid arterial flow pulsations influence the volumetric ebb and flow against soft tissue of the fairly-constrained bony cranial space. The only pathways out of shielded cranial space due to incoming arterial/CSF pressure gradients is via venous outflow and CSF outflow routes. Therefore, arterial, ICP and venous circulatory functions influence one another and the monitoring of CSF flow is also useful, in addition to the monitoring of vascular blood flow.

As shown in FIG. 8A, a user interface for monitoring venous flow and CSF aspects may appear in which facial vessels can disappear while internal cerebral-related vessels manifest. Visual landmarks, such as nose and eye placement may show. Superior sagittal sinus anatomy 810 is depicted with upward flow. The internal depth of the anatomy 810 may be represented with less precise edging. CSF movement may be shown from an upper nasal cavity via the cribriform plate or via the eye sockets, for example the optic canal that runs alongside the orbital nerve. Venous fluid flow can be shown in the sagittal sinus cavity and jugular veins. Arterial pulsing can be shown in the carotid arteries.

As shown in FIG. 8B, if a user 895 touches a region of interest 890, such as anatomy 810, the display can switch to representing driving fluidic compartments.

As shown in FIG. 8C, a deformable balloon or bob 850 construct appears superimposed over the flowing region of interest 890, such as the superior sagittal sinus, and represents pressure/volume imputed in this aspect of such a compartment, whether a venous, CSF or arterial compartment. CSF outflow 860 via the nasal cavity can also be represented. CSF fluxes at its own rate and some splits to merge into venous outflow.

User interfaces for displaying representations of electrical brain activity are shown in FIGS. 9A-9D. The selection of "Brain" mode 535 (FIG. 5A) can invoke displays relating to the brain's electrical activity. After selection, an icon 915 having a lightning bolt, or other image, may appear to indicate to the user that he or she is viewing the electrical activity mode, along with other stage icons. Synapses are mapped and represented as dots 910. The dots can represent the electrical activity of a relative area, rather than single neurons. The dots can show in different intensities and appear and fade in real time. The dots can show the net increase and decrease per vascular cycle, or per time period, or in real-time as images are continually captured of the subject's anatomy.

Figure 9A:
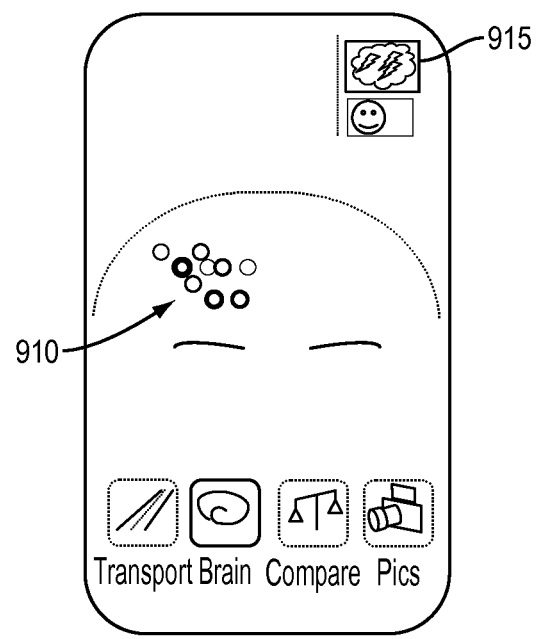
Figure 9B:
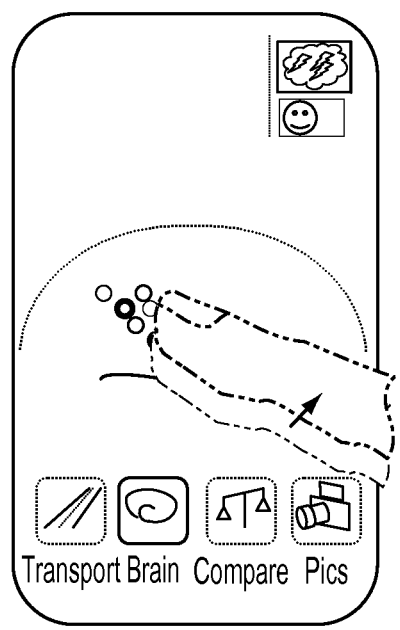

As shown in FIG. 9B, the dots 910 can be actionable by a finger-swipe to invoke a next stage. FIG. 9C illustrates the overlay of two stages of Brain modes and includes an overlay of dots 910 with an animated wave 920 representing the rippling or flux of oxygen into the fluid and tissues of the brain. The display may show the effective combination of healthy O2 delivery with a healthy pH operating environment, as both are needed for neural functioning. The combination of pH-O2 rippling can be cyclically represented in visual waves having an amplitude and timing that is synchronized with blood pulsations. The concentration of O2 and acidity of the brain is likely to vary over a cycle duration and can be represented as a gradient or gradient overlay.

If a subject has poor nutrient delivery, a slow oxygen wave 920' may appear with an alert flag 925. The colors of the display can clearly denote any problem with pH-O2 rippling in regions of risk. Regions of risk may be intermittent or time-cycle based, but may be presented as static for ease of user comprehension. Additionally, upon selection of the alert, the user may receive options to view further specifics, to check again at a later time/interval, automatically invoke the device at a later time, and/or to send the information to a medical professional.

Further specifics of pH, oxygen rippling, and energy can be displayed in details and represented with easily-comprehensible figures as shown in FIG. 10, such as thermometer-type icons or battery-type icons. In the detailed mode, pH 930, oxygen 935, and energy 940 indicators are represented separately and may be animated to show real-time changes.

An alternate user interface for representing brain health in terms of electrical activity is shown in FIGS. 11A-11D. A representation having a circuit 1105 can be displayed to the user. The circuit may have a device-level breakdown, for example, resistor-inductor-capacitor (RLC) representation, or it may have a high-level representation showing time-coupled, amplitude-dependent (wavelike) circuit equivalence. Spectroscopy can be used to compute net charge activity, Q, and can be represented by dots 1110. In turn, circuit 1105 may represent current, I, according to the equation:

$$I = \Delta Q / \text{time}$$

Cycle time information may be displayed and may be user-selectable through cycle time slider 1115. A showcased or focused display of a circuit equivalence 1105 can be displayed along with a miniature summary 1120 of what the user saw or likely processed.

Figure 11A:
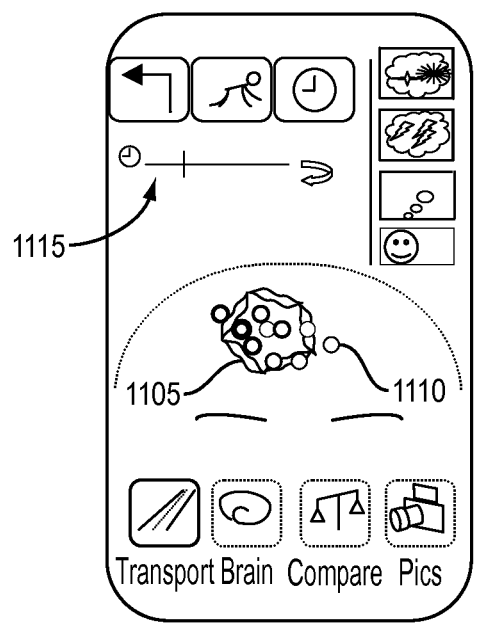
FIGS. 11A-11D are schematic illustrations of an alternate user interface for representing brain health in terms of electrical activity.
Figure 11B:
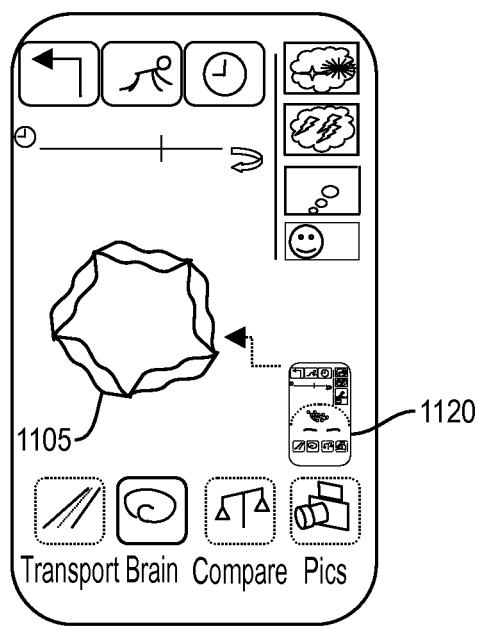
Figure 11C:
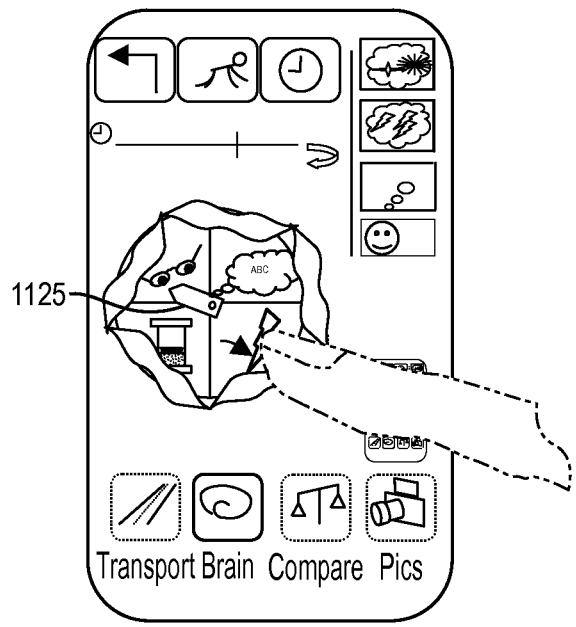
Figure 11D:
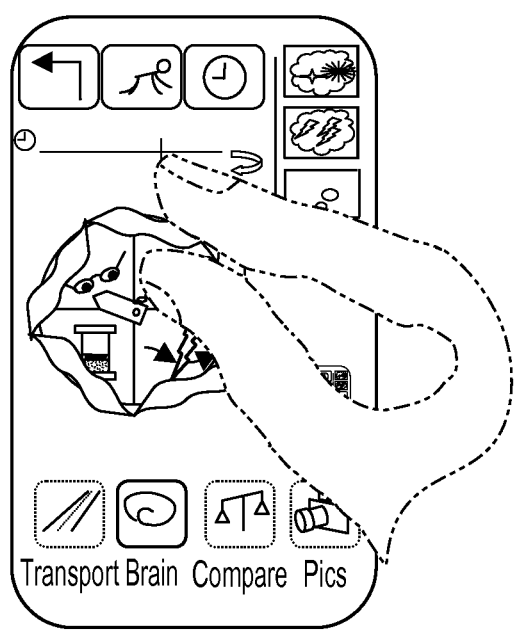

As shown in FIG. 11C, touch-activation by the user of circuit 1105 can prompt a spin-pointer 1125 selection arising in the middle of the circuit, with additional options. Alternatively, or in addition to touch-activation, the user can pinch circuit 1105, as shown in FIG. 11D, to unveil resistance equivalence for the circuit (not shown). The user can then adjust the resistance (R) values to see the impedance effects. Resistance values may correspond to stiffness of vessel walls and/or propagation delays. Visualizing the effects of resistance on brain function can help users visualize and understand how they may improve brain health through, for example, increases in metabolism.

Examples of spin-pointer selection are shown in FIG. 12, including representations for nutrient delivery 1205, energy 1210, mental attention 1215, and semantic ability 1220. A user selection of nutrient delivery 1205 can prompt, for example, detailed information pertaining to nutrient input, CO2 waste output, and the importance of H2O sufficiency. This information can help users better comprehend, for example, their calcium intake and their necessary cardiovascular/CSF flow in order to eliminate wastes. Selection of energy 1210 can prompt, for example, additional information on how the cardiovascular system transfers energy into the brain and how circulatory function relates to brain functioning. Energy information can include: educational information regarding system inter-relationship, likely trends over long periods of time, translation of newly forming circuit equivalents into changes in energy storage, and hypothetical energy deletion as it relates to loss of circuit maintenance in time.

Selection of mental attention 1215 can prompt information on attention capabilities. How the brain selects from amongst many visual stimuli, where to pay visual attention via select amplification, and what to not pay attention to can be included in this information. Selection of Semantic 1220 can prompt information on word processing. Other features relating to nutrient delivery 1205 and energy 1210 can provide additional information for the user.

Example menu items that can be activated from user-selectable options 625 or other touch controls, such as pinching, swiping, zooming are shown in Table 3. Alternatively, the device may be voice-enabled, and users may interface with the device through voice-control.

TABLE 3

| | Menu Items | | |
|---|---|---|---|
| Version | Risky Regions | Compare | Rhythms |
| 1 | Show (zoom) on high risk feed locales and/or blockages Present "what-ifs": For example, slowing effect on cyclic cycle and tidal volume after 1 min deep breathing, or hastening effect after 20 mins brief exercise | Ideal average (across all users or across age/gender) | Decompose vascular vs respiratory vs CSF frequencies/amplitudes Present "what ifs": Increase hemoglobin % uptake by say 1% Increase toxic waste % removal (CO2, lactic acid) by 1% |
| Version | Recalling It | Compare | More |
| 2 | Test My Strengths (incremental charge levels, burst rate, use working memory) | Ideal average (across all users or across age/gender) | Flag if correlation with heart attack/stroke/Alzheimer's disease |
| | MyTachometer: rpm | Ideal average (across all users or across age/gender) | Burst "density" (region per cycle time) e.g blinking stars shows degree differentiation |
| | Test My Speeds | Ideal average (across all users or across age/gender) | Show baseline energy/cycle; Prompt to forward data for research/medical purposes |
| 3 | Cycling through pyramidal-cell type tests: semantic, working memory | Mean across age/gender | Patterning response to input by age/education |
| | Patterning response to test input; classify verbal vs math, or executive functioning, or pediatrics | Versus past self-history (most recent reading/next am/day/mo/yr) | Fueling (such as ATP or glucose) |
| | Typical energy consumed when actively storing a "test" | Buddy (designate email address of another person also using the application): brain "racing" | Signaling (e.g. glutamate or CA + 2) |
| | Cumulative energy stored there via app over time | Ideal average (across all users or across age/gender) | My BrainPower: cerebral kinetic energy (KE) or KE density |
| 4 | Contrast metrics via posture (i.e. forehead below heart) | Racing/eval against a designated expert pattern: by education (e.g. SAT prep verbal/math), by field (e.g. real-time trading), by situational safety (school-based) "Health circles" w/multiple buddies or fitness partners Using relevant average, age forward a decade | Projecting next period's educational step response to input; compare actual/forecast Δ pH via bicarbonate buffering system: wave amplitudes (& frequencies for rate of response) |

Figure 13:
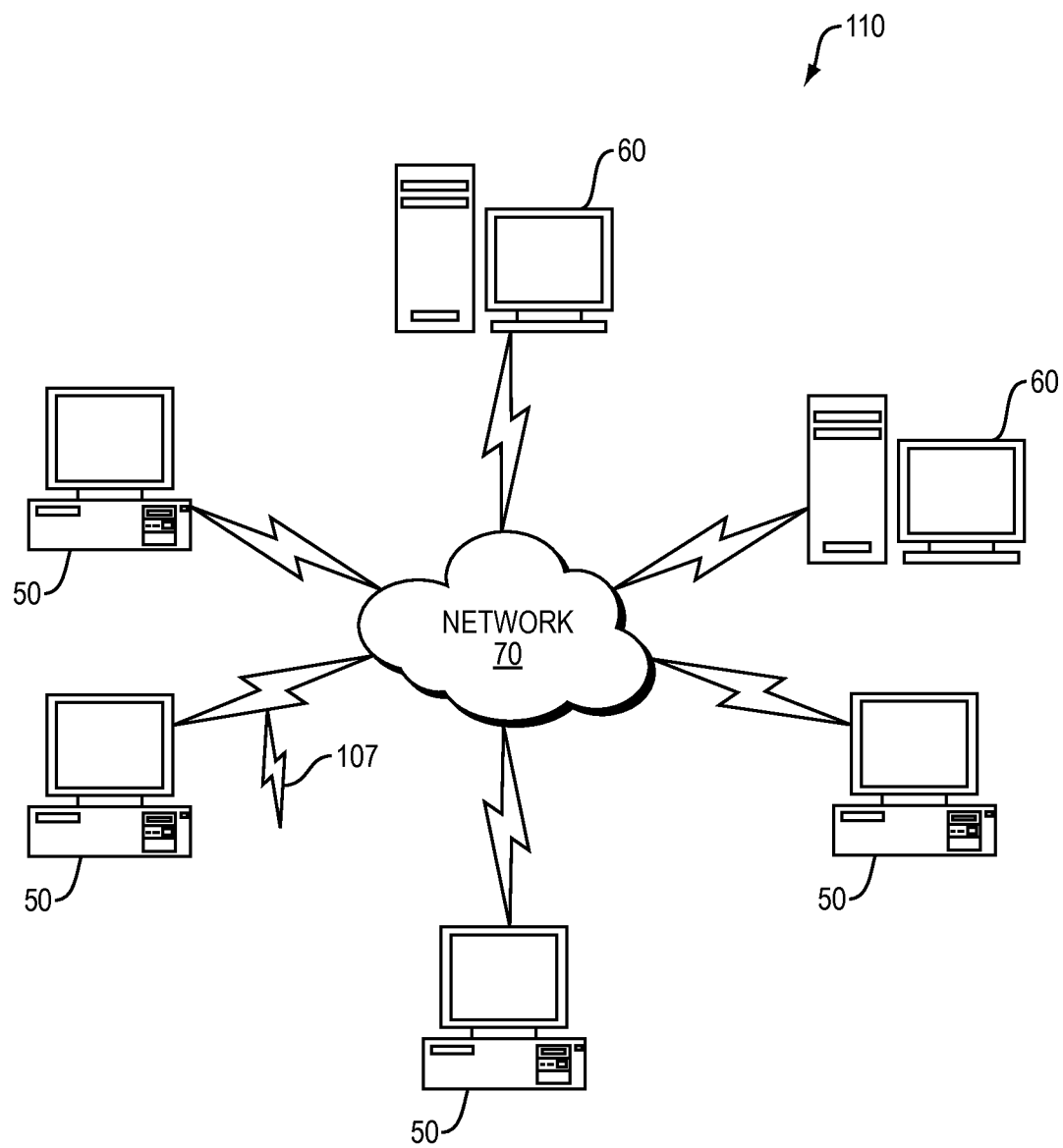
FIG. 13 is a schematic view of a computer network embodying the present invention.

FIG. 13 illustrates a computer network 110 or similar digital processing environment in which the present invention may be implemented. Mobile device or computer 50 and server computer(s) 60 provide processing, storage, and input/output devices executing application programs and the like. Mobile device or computer 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 14:
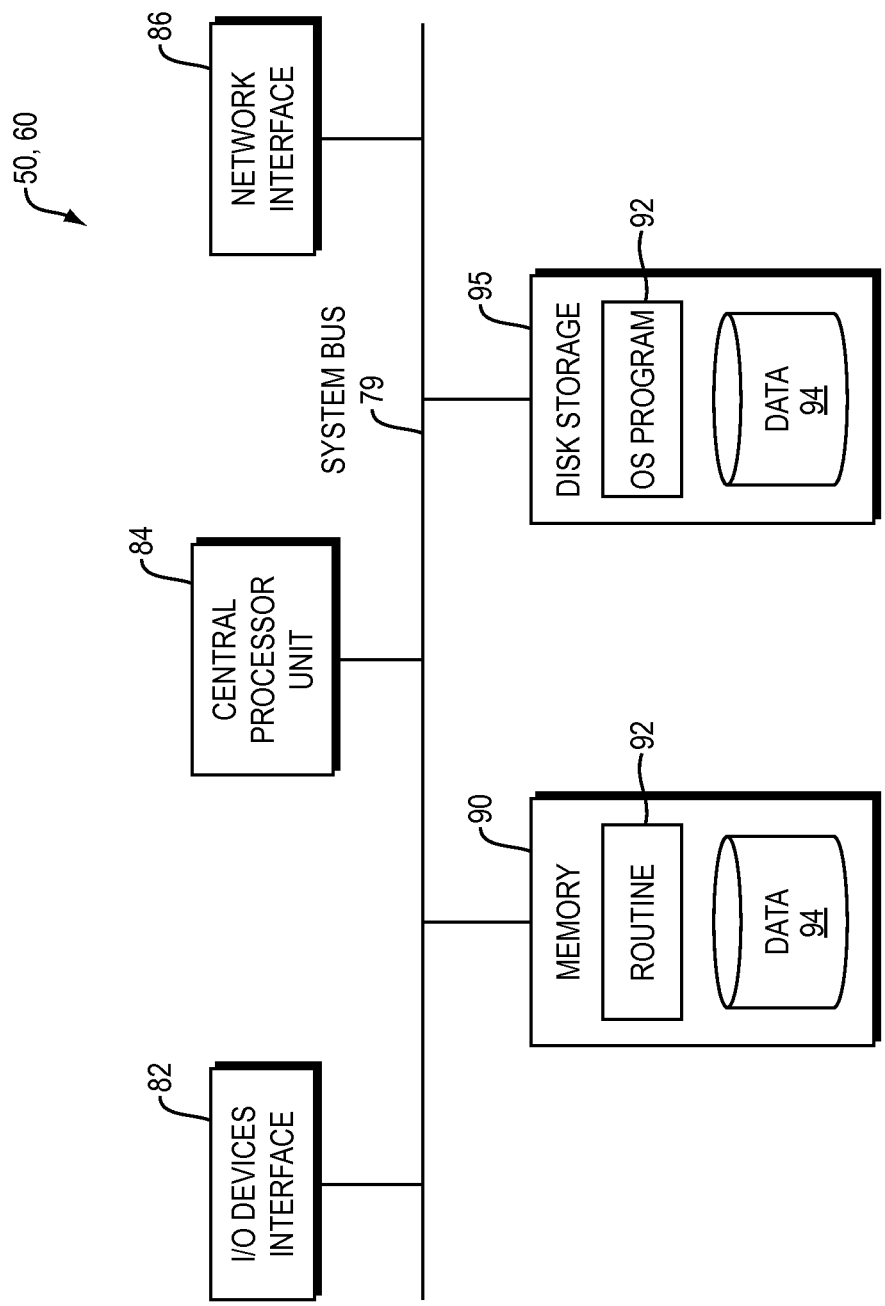
FIG. 14 is a block diagram of a computer node in the network of FIG. 13.

FIG. 14 is a diagram of the internal structure of a computer (e.g., mobile device/computer 50 or server computers 60). Mobile device or computer 50 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, microphone, displays, cameras, spectroscopy devices, wearable aids, speakers, etc.) to the computer 50, 60. Network interface 86 allows the computer to connect to various other devices attached to a network (e.g., network 70 of FIG. 13). Memory 90 provides volatile storage for computer software instructions 92 and data 94 used to implement an embodiment of the present invention (e.g., measurement module/submodules, comparator, assessment module/submodules, probability engine including evaluator and display/reporter module, and supporting code detailed above). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The advantages and objects of the invention are not necessarily encompassed by each embodiment of the invention. Those skilled in the art will recognize, or be able to ascertain using no more than routine experimentation, many equivalents to the specific embodiments described herein, which fall within the scope of the claims. The scope of the present invention is not to be limited by or to embodiments or examples described above.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided.

Articles such as "a", "an", "the" and the like, may mean one or more than one unless indicated to the contrary or otherwise evident from the context.

The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, optionally, additional unlisted elements. Only terms clearly indicative to the contrary, such as "only one of" or "exactly one of" will refer to the inclusion of exactly one element of a number or list of elements. Thus claims that include "or" between one or more members of a group are considered satisfied if one, more than one, or all of the group members are present, employed in, or otherwise relevant to a given product or process unless indicated to the contrary. Embodiments are provided in which exactly one member of the group is present, employed in, or otherwise relevant to a given product or process.

Embodiments are provided in which more than one, or all of the group members are present, employed in or otherwise relevant to a given product or process. Any one or more claims may be amended to explicitly exclude any embodiment, aspect, feature, element, or characteristic, or any combination thereof. Any one or more claims may be amended to exclude any agent, composition, amount, dose, administration route, cell type, target, cellular marker, antigen, targeting moiety, or combination thereof.

Embodiments in which any one or more limitations, elements, clauses, descriptive terms, etc., of any claim (or relevant description from elsewhere in the specification) is introduced into another claim are provided. For example, a claim that is dependent on another claim may be modified to include one or more elements or limitations found in any other claim that is dependent on the same base claim. It is expressly contemplated that any amendment to a genus or generic claim may be applied to any species of the genus or any species claim that incorporates or depends on the generic claim.

Where a claim recites a composition, methods of using the composition as disclosed herein are provided, and methods of making the composition according to any of the methods of making disclosed herein are provided. Where a claim recites a method, a composition for performing the method is provided. Where elements are presented as lists or groups, each subgroup is also disclosed. It should also be understood that, in general, where embodiments or aspects is/are referred to herein as comprising particular element(s), feature(s), agent(s), substance(s), step(s), etc., (or combinations thereof), certain embodiments or aspects may consist of, or consist essentially of, such element(s), feature(s), agent(s), substance(s), step(s), etc. (or combinations thereof). It should also be understood that, unless clearly indicated to the contrary, in any methods claimed herein that include more than one step or act, the order of the steps or acts of the method is not necessarily limited to the order in which the steps or acts of the method are recited. Any method of treatment may comprise a step of providing a subject in need of such treatment, e.g., a subject having a disease for which such treatment is warranted. Any method of treatment may comprise a step of diagnosing a subject as being in need of such treatment, e.g., diagnosing a subject as having a disease for which such treatment is warranted. Where ranges are given herein, embodiments in which the endpoints are included, embodiments in which both endpoints are excluded, and embodiments in which one endpoint is included and the other is excluded, are provided. It should be assumed that both endpoints are included unless indicated otherwise. Unless otherwise indicated or otherwise evident from the context and understanding of one of ordinary skill in the art, values that are expressed as ranges can assume any specific value or subrange within the stated ranges in various embodiments, to the tenth of the unit of the lower limit of the range, unless the context clearly dictates otherwise. "About" in reference to a numerical value generally refers to a range of values that fall within ±10%, in some embodiments ±5%, in some embodiments ±1%, in some embodiments ±0.5% of the value unless otherwise stated or otherwise evident from the context. In any embodiment in which a numerical value is prefaced by "about", an embodiment in which the exact value is recited is provided. Where an embodiment in which a numerical value is not prefaced by "about" is provided, an embodiment in which the value is prefaced by "about" is also provided. Where a range is preceded by "about", embodiments are provided in which "about" applies to the lower limit and to the upper limit of the range or to either the lower or the upper limit, unless the context clearly dictates otherwise. Where a phrase such as "at least", "up to", "no more than", or similar phrases, precedes a series of numbers, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated.

What is claimed is:

1. A method for predicting a likelihood for memory impairment in an individual, the method comprising:
    a) using a near infrared spectroscopic device on an individual at an anatomical region to be studied;
    b) determining, with the device at the anatomical region, a first measurement of at least one of an oxygen concentration ($PaO_2$), an oxygen saturation ($O_2$ sat), a hemoglobin (Hb) concentration, a carbon dioxide ($CO_2$) concentration, a carbonic acid ($H_2CO_3$) concentration, and a hydrogen ion ($H^+$) concentration at a first time;
    c) determining, with the device at the anatomical region, a second measurement of the at least one of the oxygen concentration ($PaO_2$), the oxygen saturation ($O_2$ sat), the hemoglobin (Hb) concentration, the carbon dioxide ($CO_2$) concentration, the carbonic acid ($H_2CO_3$) concentration, and the hydrogen ion ($H^+$) concentration at a second time;
    d) comparing the first measurement to the second measurement; and
    e) determining, based on step (d), a probability for one or more neurons to generate an action potential, wherein the generation of an action potential increases the probability of forming a new memory;
    thereby predicting the likelihood for memory impairment in the individual.

2. The method of claim 1, wherein the first time is a first moment or a first time interval and the second time is a second moment or a second time interval.

3. The method of claim 1, further comprising establishing a baseline from one or more measurements of the at least one of the oxygen concentration ($PaO_2$), the oxygen saturation ($O_2$ sat), the hemoglobin (Hb) concentration, the carbon dioxide ($CO_2$) concentration, the carbonic acid ($H_2CO_3$) concentration, and the hydrogen ion ($H^+$) concentration at the first time, wherein the baseline represents a memory map of the individual.

4. The method of claim 3, further comprising normalizing the memory map based on the individual's age, gender, or other characteristic.

5. The method of claim 1, further comprising assessing hypoxia, acidosis, or a combination thereof, based on steps (a)-(c), wherein a presence of hypoxia, acidosis, or combination thereof relates to an increased likelihood of memory impairment.

6. The method of claim 5, wherein the first and second measurements include at least one of oxygen concentration ($PaO_2$), oxygen saturation ($O_2$ sat), hemoglobin (Hb) concentration, and carbon dioxide ($CO_2$) concentration, and the presence of hypoxia is determined based on the first and second measurements.

7. The method of claim 5, wherein the first and second measurements include at least one of carbonic acid ($H_2CO_3$)

concentration and hydrogen ion (H$^+$) concentration, and the presence of acidosis is determined based on the first and second measurements.

8. The method of claim 1, further comprising measuring cerebral blood pressure, cerebral blood flow, cerebrospinal fluid pressure, cerebrospinal fluid flow, intracranial pressure, or combinations thereof.

9. The method of claim 1, wherein the region comprises a forehead of the individual.

10. The method of claim 1, wherein the region comprises a frontal, parietal, occipital, limbic, or temporal lobe of the individual.

11. The method of claim 1, wherein the device is a portable device, such as a cell phone, tablet, laptop computer, or wearable aid.

12. The method of claim 1, wherein the device comprises a camera and software for measuring the one or more ions, one or more molecules, or combinations thereof.

13. A computer system to predict a likelihood for memory impairment in an individual, the system comprising:
- a measuring module configured to determine a first measurement of at least one of an oxygen concentration (PaO$_2$), an oxygen saturation (O$_2$ sat), a hemoglobin (Hb) concentration, a carbon dioxide (CO$_2$) concentration, the carbonic acid (H$_2$CO$_3$) concentration, and the hydrogen ion (H$^+$) concentration at a first time; and configured to determine a second measurement of the at least one of the oxygen concentration (PaO$_2$), the oxygen saturation (O$_2$ sat), the hemoglobin (Hb) concentration, the carbon dioxide (CO$_2$) concentration, the carbonic acid (H$_2$CO$_3$) concentration, and the hydrogen ion (H$^+$) concentration at a second time;
- a comparison module configured to receive and compare the first measurement to the second measurement; and
- a probability module coupled to the comparison module and configured to determine a probability for one or more neurons to generate an action potential, wherein the generation of an action potential increases the probability of forming a new memory;
- from the determined probability, the probability module forming a prediction of the likelihood for memory impairment in the individual.

14. The computer system of claim 13, wherein the first time is a first moment or a first time interval and the second time is a second moment or a second time interval.

15. The computer system of claim 13, further comprising a baseline module responsive to the measuring module and configured to establish a baseline from one or more measurements of the at least one of the oxygen concentration (PaO$_2$), the oxygen saturation (O$_2$ sat), the hemoglobin (Hb) concentration, the carbon dioxide (CO$_2$) concentration, the carbonic acid (H$_2$CO$_3$) concentration, and the hydrogen ion (H$^+$) concentration at the first time, wherein the baseline represents a memory map of the individual.

16. The computer system of claim 15, further comprising a normalization module configured to normalize the memory map based on the individual's age, sex, or other characteristic.

17. The computer system of claim 13, further comprising an assessment module responsive to the measuring module and configured to assess hypoxia, acidosis, or a combination thereof, wherein a presence of hypoxia, acidosis, or combination thereof relates to an increased likelihood for memory impairment.

18. The computer system of claim 17, wherein the first and second measurements include at least one of oxygen concentration (PaO$_2$), oxygen saturation (O$_2$ sat), hemoglobin (Hb) concentration, and carbon dioxide (CO$_2$) concentration, and the presence of hypoxia is determined based on the first and second measurements.

19. The computer system of claim 17, wherein the first and second measurements include at least one of carbonic acid (H$_2$CO$_3$) concentration and hydrogen ion (H$^+$) concentration, and the presence of acidosis is determined based on the first and second measurements.

20. The computer system of claim 13, further comprising a second measuring module configured to measure cerebral blood pressure, cerebral blood flow, cerebrospinal fluid pressure, cerebrospinal fluid flow, intracranial pressure, or combinations thereof.

21. The computer system of claim 13, further comprising a device module configured to connect one or more infrared spectroscopic devices operatively coupled to the measuring module.

22. The computer system of claim 21, wherein the infrared spectroscopic device is a portable device, such as a cell phone, tablet, laptop computer, or wearable aid.

23. The computer system of claim 21, wherein the infrared spectroscopic device comprises a camera and is configured to measure the one or more ions, one or more molecules, or combinations thereof.

* * * * *